(12) United States Patent
Tal et al.

(10) Patent No.: US 7,621,276 B2
(45) Date of Patent: Nov. 24, 2009

(54) INTRAUTERINE FALLOPIAN TUBE OCCLUSION DEVICE

(75) Inventors: Michael G. Tal, Woodbridge, CT (US);
Patrick N. Gutelius, Monroe, CT (US);
Mark J. DeBisschop, Burlington, CT (US); Oleg Shikhman, Trumbull, CT (US)

(73) Assignees: Yale University, New Haven, CT (US); Cantramed, LLC, Charlotte, NC (US)

( * ) Notice: Subject to any disclaimer, the term of this patent is extended or adjusted under 35 U.S.C. 154(b) by 66 days.

(21) Appl. No.: 11/892,560

(22) Filed: Aug. 23, 2007

(65) Prior Publication Data

US 2008/0047563 A1 Feb. 28, 2008

Related U.S. Application Data

(63) Continuation-in-part of application No. 11/884,027, filed as application No. PCT/US2006/005245 on Feb. 15, 2006.

(60) Provisional application No. 60/653,743, filed on Feb. 15, 2005.

(51) Int. Cl.
*A61F 6/06* (2006.01)

(52) U.S. Cl. .................................... 128/831; 128/830

(58) Field of Classification Search .......... 128/830–840
See application file for complete search history.

(56) References Cited

U.S. PATENT DOCUMENTS

| 3,405,711 | A |   | 10/1968 | Bakunin |         |
|-----------|---|---|---------|---------|---------|
| 3,659,596 | A | * | 5/1972  | Robinson | 128/833 |
| 3,687,129 | A | * | 8/1972  | Nuwayser | 128/843 |
| 3,704,704 | A |   | 12/1972 | Gonzales |         |
| 3,789,838 | A |   | 2/1974  | Fournier |         |
| 3,805,767 | A |   | 4/1974  | Erb     |         |
| 3,918,443 | A |   | 11/1975 | Vennard et al. |  |
| 4,353,363 | A | * | 10/1982 | Sopena Quesada | 128/833 |
| 4,537,186 | A | * | 8/1985  | Verschoof et al. | 128/831 |
| 4,612,924 | A |   | 9/1986  | Cimber  |         |
| 4,628,924 | A | * | 12/1986 | Cimber  | 128/839 |
| 4,932,421 | A |   | 6/1990  | Kaali et al. |    |
| 5,095,917 | A | * | 3/1992  | Vancaillie | 128/831 |
| 5,146,931 | A |   | 9/1992  | Kurz    |         |
| 5,555,896 | A | * | 9/1996  | Cimber  | 128/830 |

(Continued)

FOREIGN PATENT DOCUMENTS

WO      WO2006/088909        8/2006

*Primary Examiner*—Kim M Lewis
(74) *Attorney, Agent, or Firm*—Welsh & Flaxman LLC

(57) ABSTRACT

An occlusion device for actively occluding orifices of fallopian tubes includes a resilient body having an elongated member with a first end and a second end. The elongated member further includes a first leg ending with the first end of the elongated member, a second leg ending with the second end of the elongated member and a connection member positioned therebetween. A first orifice plug is secured at the first end of the elongated member and a second orifice plug is secured at the second end of the elongated member. The first and second orifice plugs are shaped and dimensioned to seat at the orifices of the fallopian tubes or within the fallopian tubes as the elongated member spreads outwardly with the first end and second end moving apart. A delivery device for delivery of medication or therapeutic agents to a uterine cavity is also disclosed.

73 Claims, 27 Drawing Sheets

U.S. PATENT DOCUMENTS

| | | | |
|---|---|---|---|
| 5,935,137 A * | 8/1999 | Saadat et al. | 606/135 |
| 6,042,030 A * | 3/2000 | Howe et al. | 239/703 |
| 6,346,102 B1 | 2/2002 | Harrington et al. | |
| 6,705,323 B1 | 3/2004 | Nikolchex et al. | |
| 2002/0198547 A1 | 12/2002 | Schultz | |
| 2003/0066533 A1 | 4/2003 | Loy | |
| 2004/0009205 A1 * | 1/2004 | Sawhney | 424/423 |
| 2005/0125022 A1 | 6/2005 | Ravikumar et al. | |
| 2005/0192616 A1 | 9/2005 | Callister et al. | |
| 2008/0302368 A1 * | 12/2008 | McGuckin et al. | 128/831 |

* cited by examiner

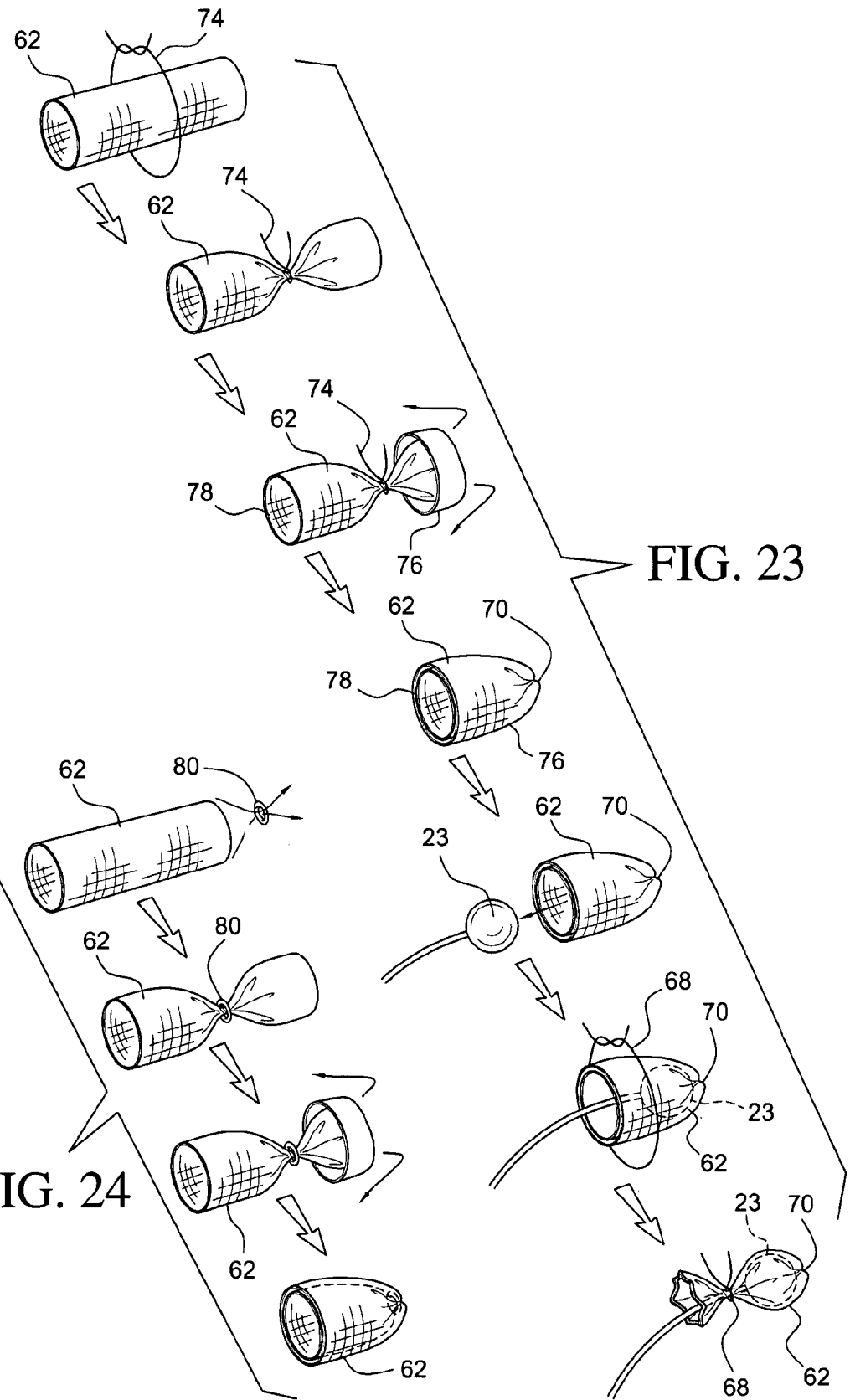

INTRAUTERINE FALLOPIAN TUBE OCCLUSION DEVICE

CROSS REFERENCE TO RELATED APPLICATIONS

This application is continuation-in-part of U.S. patent application Ser. No. 11/884,027, filed Aug. 9, 2007, entitled "INTRAUTERINE FALLOPIAN TUBE OCCLUSION DEVICE AND METHOD FOR USE", which is currently pending, which is the National Stage of International Application No. PCT/US2006/005245, filed Feb. 15, 2006, entitled "INTRAUTERINE FALLOPIAN TUBE OCCLUSION DEVICE AND METHOD FOR USE", which claims the benefit of U.S. Provisional Patent Application Ser. No. 60/653,743, filed Feb. 15, 2005, entitled "INTRAUTERINE FALLOPIAN TUBE OCCLUSION DEVICE".

BACKGROUND OF THE INVENTION

1. Field of the Invention

The invention relates to a fallopian tube occlusion device and method for use. More particularly, the invention relates to a fallopian tube occlusion device that uses the unique shape of the uterine cavity to ensure delivery and proper positioning thereof through the application of barrier members specifically structured for seating within the uterus and/or fallopian tube anatomy in a manner creating a barrier. The invention also relates to a delivery mechanism utilizing the device described herein to deliver medication and/or other therapeutic agents to the uterus and/or fallopian tube anatomy.

2. Description of the Related Art

Several types of intrauterine devices (IUDs) are available and used worldwide. There are inert IUDs, copper IUDs and hormone impregnated IUDs. There is ongoing controversy regarding the mechanisms of action of IUDs in humans. Classically, the view was that the IUD in humans acted predominantly after fertilization to prevent implantation, but evidence has accumulated for some effects before fertilization. As a general rule, the pre-fertilization effects are not enough to prevent fertilization and, therefore, the post-fertilization effects are most important. The post-fertilization mechanisms of action of the IUD include slowing or speeding the transport of the early embryo through the fallopian tube, damage to or destruction of the early embryo before it reaches the uterus, and prevention of implantation. This mechanism of action is perceived as an early abortion by some, and prevents many patients from using IUDs as a temporary mode of contraception. Another problem with IUDs is expulsion from the uterus and subsequent unwanted pregnancy. Other potential complications of IUDs are uterine infection, uterine perforation and most important ectopic pregnancy. Ectopic pregnancy is a condition where the embryo has implanted outside of the uterine cavity, usually in the fallopian tube. This condition is also hazardous to the patient and can lead to internal bleeding and severe morbidity and even mortality. This potential complication also deters patients from the use of IUDs.

Another problem affecting many women is endometriosis. One of the proposed mechanisms of endometriosis is flow of the menstrual blood through the fallopian tubes into the peritoneal cavity. This condition usually affects younger patients and permanent tubal ligation or occlusion is not warranted. It is thought that temporary tubal occlusion might prevent the flow of blood through the fallopian tubes and into the peritoneal cavity and thus might improve the patient's symptoms.

Fallopian tube ligation is usually performed surgically. Transvaginal tubal occlusion has also been described before. There are several methods of tubal ligation and occlusion.

With the foregoing in mind, a need exists for an improved intrauterine system replacing currently marketed IUDs and other methods of contraception, such as, tubal ligation.

SUMMARY OF THE INVENTION

It is, therefore, an object of the present invention to provide an occlusion device for actively occluding orifices of fallopian tubes using the shape of a uterine cavity as a guide to proper positioning of the occlusion device. The occlusion device includes a resilient body having an elongated member with a first end and a second end. The elongated member further includes a first leg ending with the first end of the elongated member, a second leg ending with the second end of the elongated member and a connection member positioned therebetween. A first orifice plug is secured at the first end of the elongated member and a second orifice plug is secured at the second end of the elongated member. The first and second orifice plugs are shaped and dimensioned to seat at the orifices of the fallopian tubes or within the fallopian tubes as the elongated member spreads outwardly with the first end and second end moving apart.

It is also an object of the present invention to provide an occlusion device wherein the connection member is substantially circular with a first end connected to the first leg and a second end connected to the second leg.

It is also another object of the present invention to provide an occlusion device wherein the first orifice plug is spherical and the second orifice plug is spherical.

It is also a further object of the present invention to provide an occlusion device wherein the resilient body is preferably made from a shaped memory alloy metal.

It is another object of the present invention to provide an occlusion device wherein the first orifice plug and the second orifice plug each include a tissue in-growth member.

It is a further object of the present invention to provide an occlusion device wherein the tissue in-growth member is a fabric sock.

It is still another object of the present invention to provide an occlusion device wherein the first orifice plug and the second orifice plug each are impregnated with a medication.

It is yet another object of the present invention to provide an occlusion device wherein the first and second orifice plugs are selectively separated from the resilient body.

It is also a further object of the present invention to provide an occlusion device wherein the connection member is a spring biased loop.

It is also an object of the present invention to provide an occlusion device wherein the first orifice plug and the second orifice plug are shaped like a flying saucer.

It is another object of the present invention to provide an occlusion device wherein the first orifice plug and the second orifice plug are football-shaped.

It is a further object of the present invention to provide an occlusion device wherein the first orifice plug and the second orifice plug are bell-shaped.

It is also an object of the present invention to provide an occlusion device wherein the first orifice plug and the second orifice plug each include multiple tapered ring members.

It is also another object of the present invention to provide an occlusion device wherein the first orifice plug and the second orifice plug each include a rounded tip and an outwardly tapering wall with a thin pliable flange at a proximal end thereof.

It is also a further object of the present invention to provide an occlusion device wherein the first orifice plug and the second orifice plug each have a prolate spheroid shape.

It is also an object of the present invention to provide an occlusion device wherein the first orifice plug and the second orifice plug are each manufactured from an elastic material which expands or contracts upon placement in the fallopian tube.

It is still a further object of the present invention to provide an occlusion device wherein the first orifice plug and the second orifice plug each include a ball and socket arrangement.

It is yet a further object of the present invention to provide an occlusion device wherein the first orifice plug and the second orifice plug each include an inner portion made from a relatively hard material and an outer soft pliable material is affixed over the inner portion.

It is also an object of the present invention to provide an occlusion device wherein the first orifice plug and the second orifice plug each include a hard outer shell composed of a bioabsorbable material which quickly dissolves upon deployment within the fallopian tube.

It is another object of the present invention to provide an occlusion device wherein the first orifice plug and the second orifice plug each include tissue in-growth promoting whiskers.

It is also a further object of the present invention to provide an occlusion device wherein the first orifice plug and the second orifice plug each include tissue in-growth promoting loops.

It is also an object of the present invention to provide a delivery device for delivery of medication or therapeutic agents to a uterine cavity.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 21, 22, 23 and 24 show the steps associated with various techniques for the application of a tissue in-growth member to the orifice plug.

DESCRIPTION OF THE PREFERRED EMBODIMENTS

Figure 1:
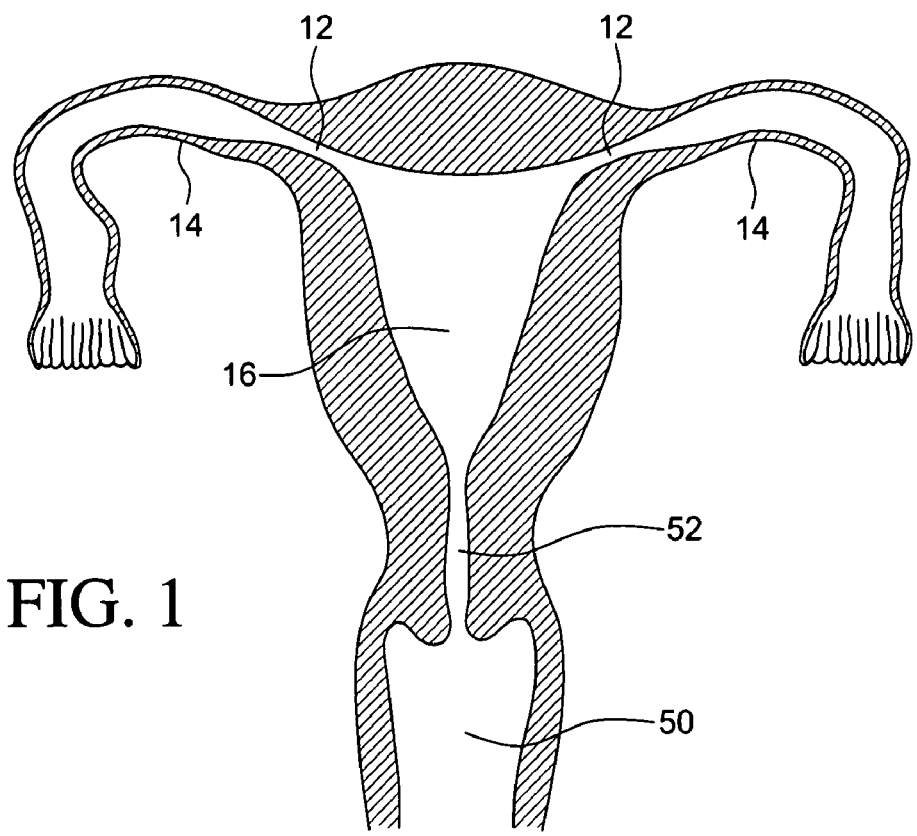
FIGS. 1 to 6 are various views showing delivery of the occlusion device in accordance with the present invention.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention. Since various embodiments are disclosed herein, similar reference numerals have been employed throughout the present disclosure when referring to similar elements in the various embodiments.

With reference to the various figures, an occlusion device 10 in accordance with a preferred embodiment of the present invention is disclosed that will actively occlude the orifices 12 of the fallopian tubes 14 using the shape of the uterine cavity 16 as a guide to the proper positioning of the occlusion device 10. The shape of the uterine cavity 16 is illustrated in FIG. 1. The uterine cavity 16 is normally in continuation with the fallopian tubes 14. For fertilization, the sperm migrates from the uterine cavity 16 into the fallopian tube 14. Occlusion of the fallopian tube 14 prevents fertilization by preventing migration of the sperm into the fallopian tube 14.

The present invention provides an occlusion device 10 that enables tubal occlusion, either permanent or temporary, utilizing the unique shape of the uterine cavity 16. This occlusion device 10 has the potential for a reduced rate of tubal pregnancy and, therefore, may be used by a larger patient population, including those that are adamantly opposed to abortion. The present invention also allows nonsurgical tubal occlusion that can be done as an office procedure and without the need for surgery or the necessity for visualization of the fallopian tube orifices either radiologically, ultrasonically, or with a hysteroscope. The present invention also provides a treatment option for women that suffer from endometriosis, an often debilitating disease that commonly affects younger women. The present occlusion device 10 uses radial force and inherent properties in its construction to prevent migration or expulsion of the occlusion device 10. As such, the present invention may be used with the following procedures: contraception, either permanent or temporary; treatment of endometriosis; and potentially treatment of other causes of abnormal uterine bleeding or pelvic pain. The present device 10 may be adaptable to other therapies or treatments, such as localized medicinal delivery, with only an alteration to the barrier system.

In accordance with a preferred embodiment, the unique shape of the uterine cavity 16 allows the present occlusion device 10 to be inserted without (or with) visualization into the uterine cavity 16 for positioning in a manner that occludes entry into the fallopian tubes 14. The unique shape also maintains the occlusion device 10 in place without the need for sutures or any other anchoring mechanism. The present occlusion device 10 is also readily removable and prevents migration of the sperm into the fallopian tube 14, thereby preventing fertilization. The presence of the occlusion device 10 in the uterine cavity 16 also redundantly acts as an IUD, but the occlusion effects prevent fertilization and thereby avert the destruction of an embryo, which is considered the major mechanism of an IUD's birth control efficacy. This makes the present occlusion device 10 more acceptable to patients and allows its use in a larger part of the population.

As mentioned above, the present occlusion device 10 functions primarily as an occluding structure for the orifices 12 of the fallopian tubes 14 and secondarily as an IUD. The present invention also relates to a method and apparatus for transvaginal implantation and removal of the occlusion device 10.

Figure 14:
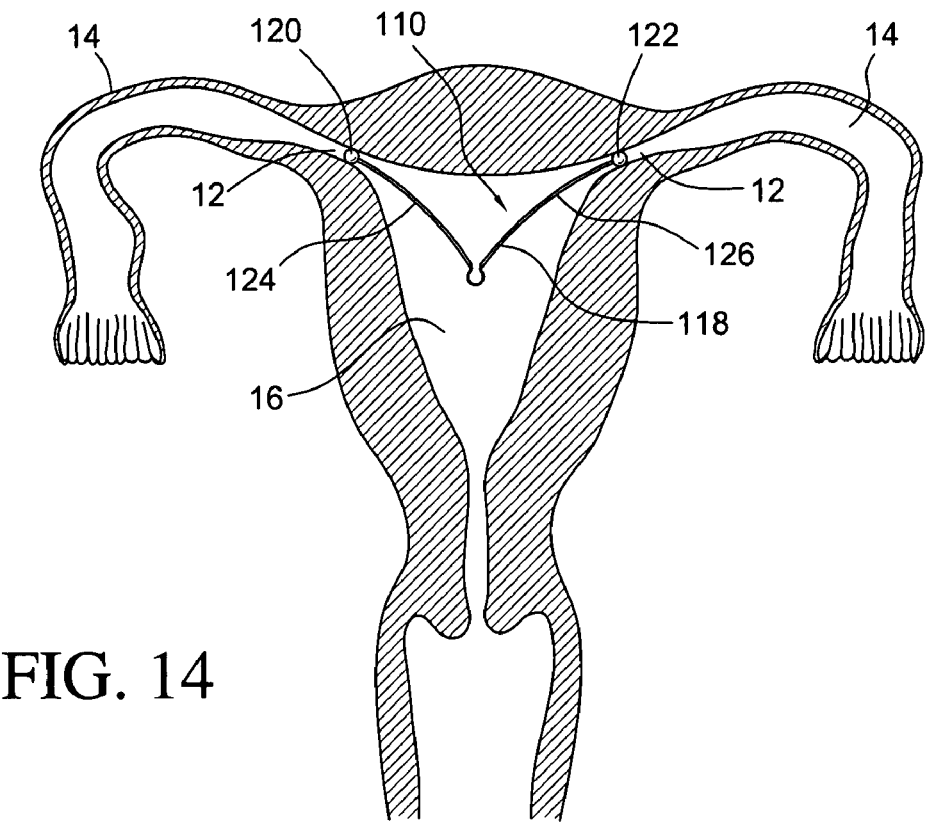
FIGS. 14, 15 and 16 are various views showing delivery of an alternate embodiment in which the orifice plugs are selectively detachable from the elongated member.
Figure 15:
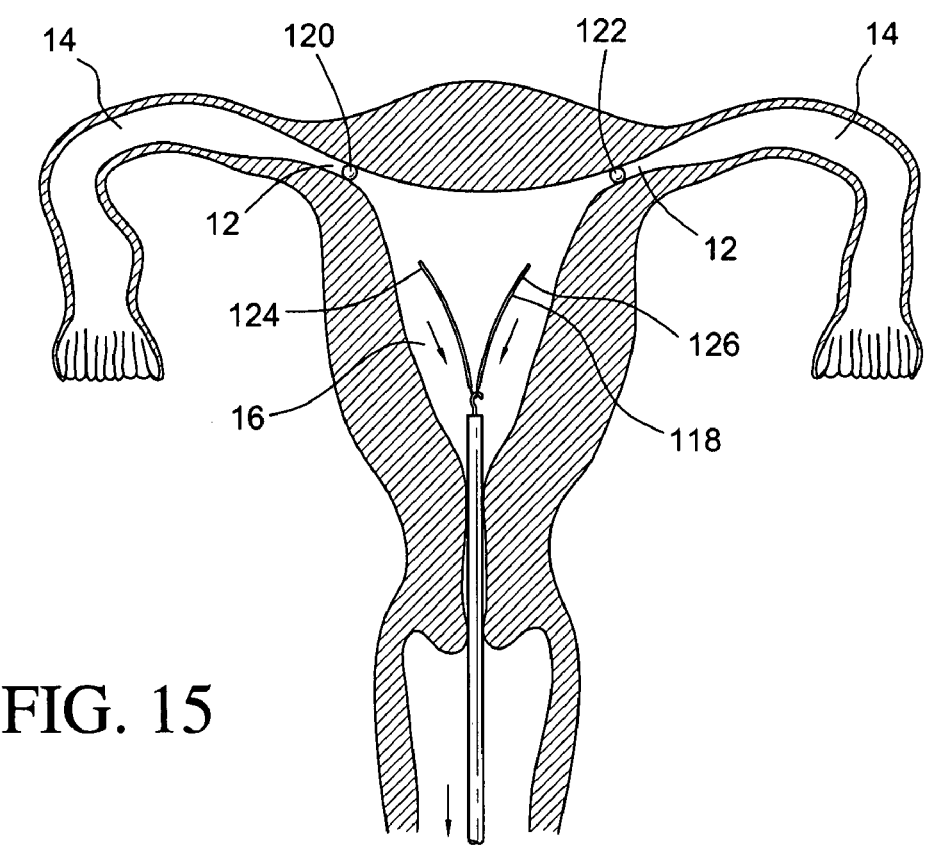
Figure 16:
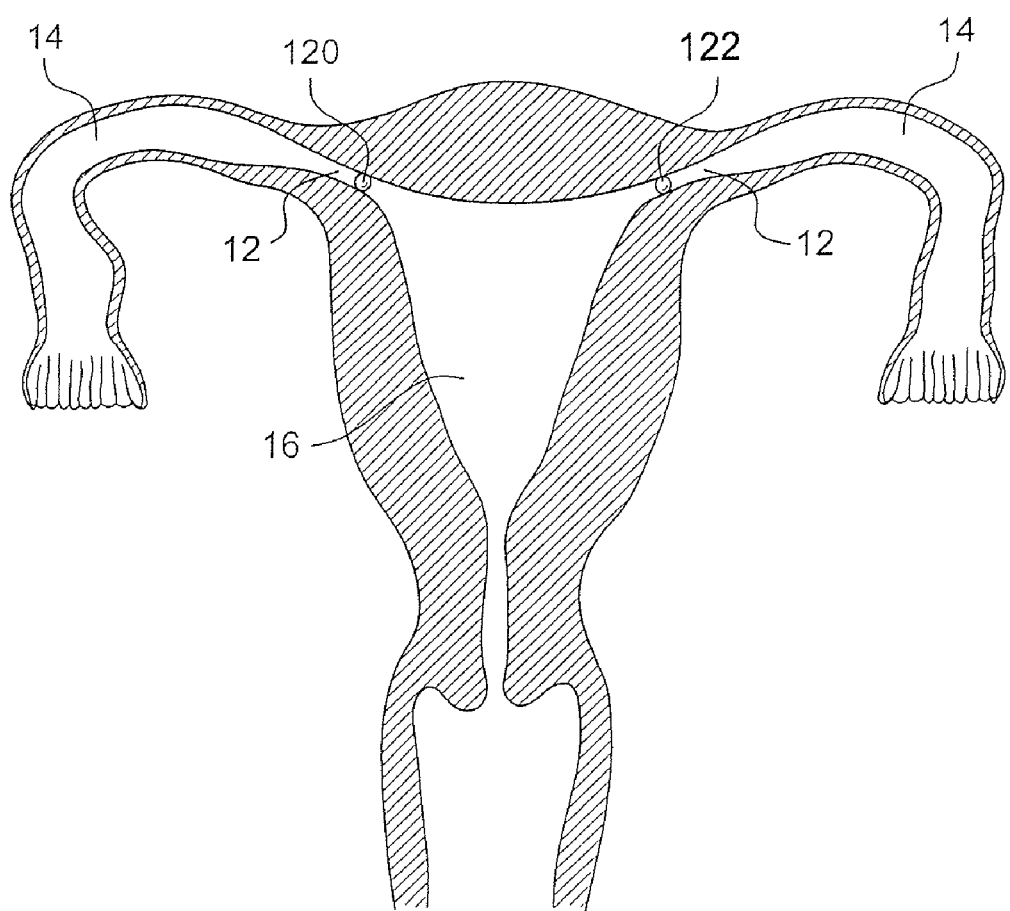

As is discussed below in greater detail, the present occlusion device 10 is composed of a resilient body 18 with first and second orifice plugs 20, 22 at the respective first and second ends 24, 26 thereof. The resilient body 18 is preferably made from a shaped memory alloy metal (such as, Nitinol) or any other material (or combination of materials) that will provide appropriate continuous lateral pressure. The orifice plugs 20, 22 for the fallopian tubes 14 can be made from various materials such as metals, plastics, elastomers such as silicone, or combinations thereof, and be impregnated with various medications and compounds. In addition to generally molded constructions, the orifice plugs 20, 22 may take the form of a mesh or coil with or without a tissue in-growth member (for example, of a mesh material) for anchoring to surrounding tissue. The resilient body 18 and/or orifice plugs 20, 22 can be either inert, meaning without any medication or substance on them, or released from them, or they can be impregnated with any medication such as hormones or metal, such as, copper. The orifice plugs 20, 22 can also be covered with any other kind of spermicide or other materials. As a result, the present device 10 may be used as a medication delivery device, supplying medication to specific locations and then being retrieved as discussed below with reference to FIGS. 8-13 or maintained in position as discussed below with reference to FIGS. 14, 15 and 16.

The present occlusion device 10 can also serve as a delivery system for the orifice plugs 20, 22 or any occlusion or other devices to the orifices 12 of the fallopian tubes 14. The occlusion device 10 utilizes the shape of the uterine cavity 16 and conforms the shape of the first and second orifice plugs 20, 22 to the orifices 12 of the fallopian tubes 14. As briefly mentioned above, the orifice plugs 20, 22 can contain any kind of material or medicine to be delivered into the orifices 12 or the fallopian tubes 14. Once the material or medicine is delivered to the orifices 12 or the fallopian tubes 14, the occlusion device 10 can be removed in the manner discussed below with reference to FIGS. 8 to 13, or the first and second orifice plugs 120, 122 may be selectively separated from the resilient body 118 and left in place within the orifices 12 of the fallopian tubes 14 as discussed below with reference to the embodiment disclosed with reference to FIGS. 14, 15 and 16.

Referring to the various figures, and in accordance with a preferred embodiment of the present invention, the present occlusion device 10 includes a resilient body 18 exhibiting spring-like characteristics having first and second orifice plugs 20, 22 secured at opposite ends thereof. The first and second orifice plugs 20, 22 are shaped and dimensioned to ride up the walls of the uterine cavity 16 until they seat within the orifices 12 of the fallopian tubes 14, within the fallopian tubes 14 or partially within the orifices 12 of the fallopian tubes 14 and partially with the fallopian tubes 14 as the resilient body 18 spreads outwardly with the first end 24 and second end 26 thereof moving apart.

More particularly, the resilient body 18 includes an elongated member 28 having a first end 30 and a second end 32. The first end 30 of the elongated member 28 is composed of a first leg 34 and the second end 32 of the elongated member 28 is composed of a second leg 36. The first orifice plug 20 is secured at the distal end of the first end 30 of the elongated member 28 and the second orifice plug 22 is secured at a distal end of the second end 32 of the elongated member 28.

The first leg 34 includes a first end 38 and second end 40, and the second leg 36 includes a first end 42 and second end 44. The first ends 38, 42 of the respective first and second legs 34, 36 are respectively connected, while the second ends 40, 44 of the first and second legs 34, 36 are respectively free and are provided with, and coupled to, the respective first and second orifice plugs 20, 22. A connection member 37 resiliently couples the first ends 38, 42 of the first and second legs 34, 36 in a manner biasing the second ends 40, 44 of the first and second legs 34, 36 from each other when they are not restrained in a manner discussed below in greater detail.

Figure 7A:
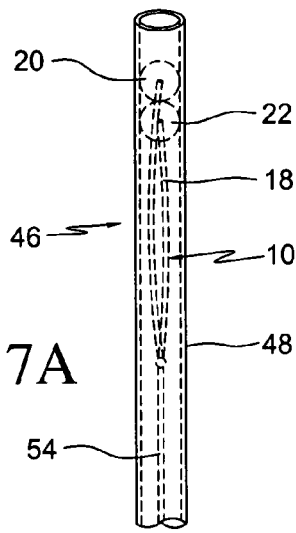
FIGS. 7A to 7D are detailed views showing the delivery apparatus for use in accordance with the present invention with the steps of forcing the occlusion device from within a container via a delivery rod.
Figure 7B:
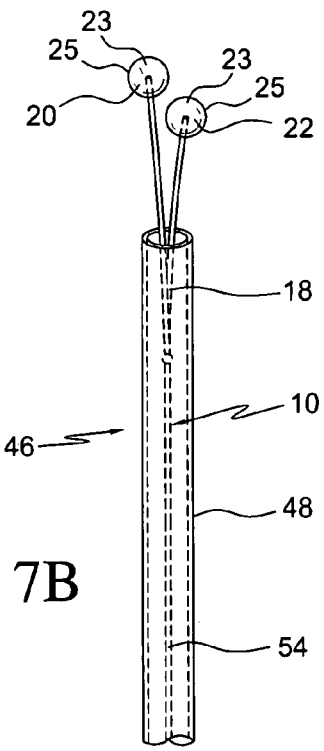
Figure 7C:
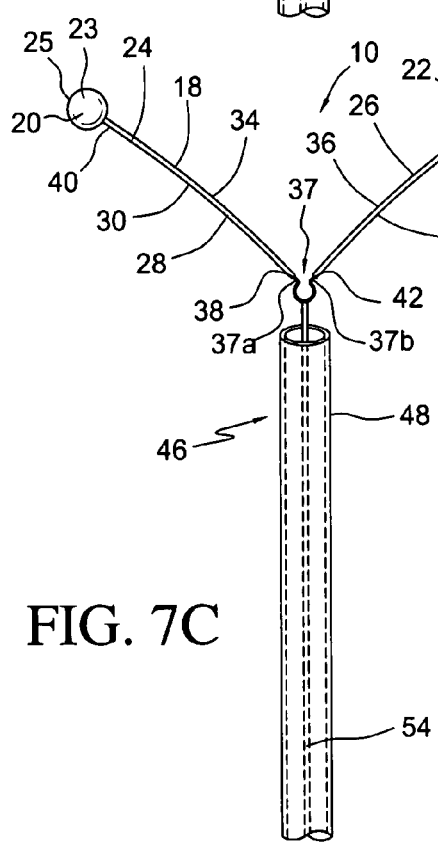
Figure 7D:
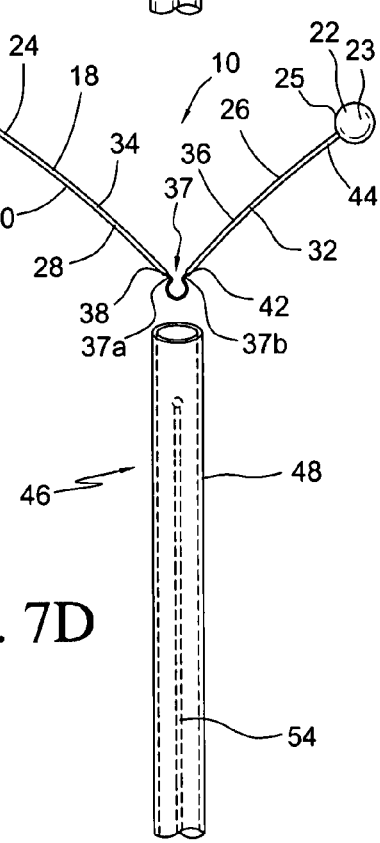
Figure 8:
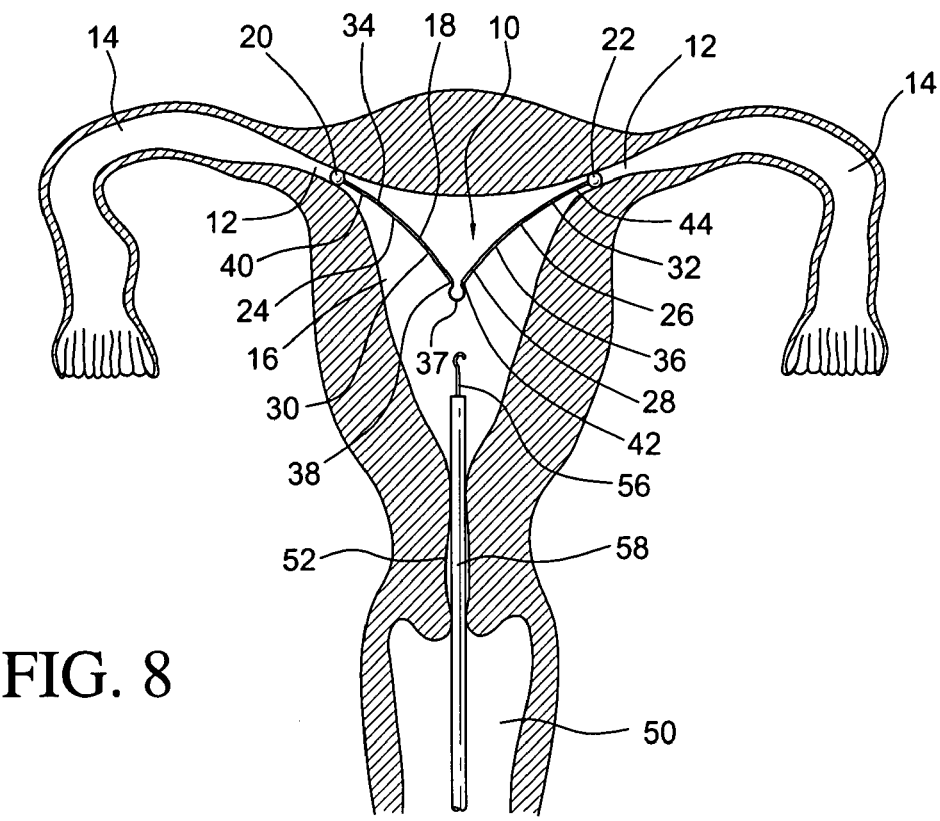
FIGS. 8 to 13 are various views showing retrieval of the present occlusion device.

With this in mind, the first leg 34 and the second leg 36 are angularly oriented relative to each other creating an elongated member 28 which is substantially V-shaped when the first leg 34 and the second leg 36 are allowed to move away from each other based upon the outward bias inherent in the connection member 37 between the first and second legs 34, 36. The inherent bias in the connection member 37 is created through the utilization of spring materials or shape memory materials in the construction of the resilient body 18, in particular, the connection member 37. With this in mind, the connection member 37 includes a substantially circular configuration with a first end 37a connected to the first end 38 of the first leg 34 and a second end 37b connected to the first end 42 of the second leg 36 (see FIGS. 7C and 7D). The connection member 37 is formed with an inherent outward bias that forces the first leg 34 and the second leg 36 outwardly upon deployment.

In addition, and in accordance with a preferred embodiment, the first leg 34 and the second leg 36 are formed with an outward bow when fully extended. This outward bow stores further outward bias when the occlusion device 10 is compressed for storage and deployment. In accordance with a preferred embodiment, when the occlusion device 10 is entirely unrestrained the first and second legs 34, 36 will form a maximum angle of approximately 150 degrees. This angle forms a geometry preventing the first and second legs 34, 36 from moving away from a fundamentally centralized location in the uterine cavity 16 (see FIGS. 1 to 6). That is, the shape of the resilient body 18, a sort of triangle, only spreads so wide so that it would bump into the walls of the uterine cavity 16, that way staying located in the center of the uterine cavity 16. If in contrast to the present invention the resilient body were straight, it could then more easily migrate laterally deeper into one fallopian tube and become un-plugged from the opposite side.

Figure 17A:
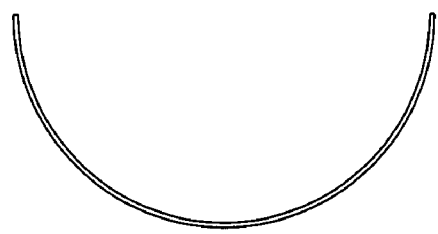
FIGS. 17A, 17B, 17C and 17D show various shapes of an elongated member that may be used in accordance with the present invention.
Figure 17B:
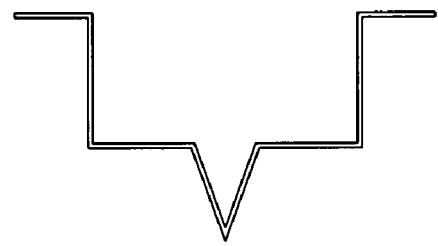
Figure 17C:
Figure 17D:
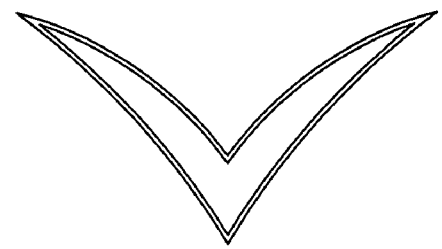

Although a preferred embodiment of the present invention employs a V-shaped elongated member with an outward bow as disclosed above, it is contemplated the elongated member 28 may be formed with a variety of shapes (whether in a fundamentally two dimensional planar configuration or a three dimensional planar configuration) so long as it retains its spring-like properties. Examples of contemplated shapes are shown in FIGS. 17A to 17D: FIG. 17A shows a U-shaped elongated member; FIG. 17B shows a stepped elongated member; FIG. 17C shows a crescent-shaped elongated member; and FIG. 17D shows a chevron-shaped elongated member.

Figure 18:
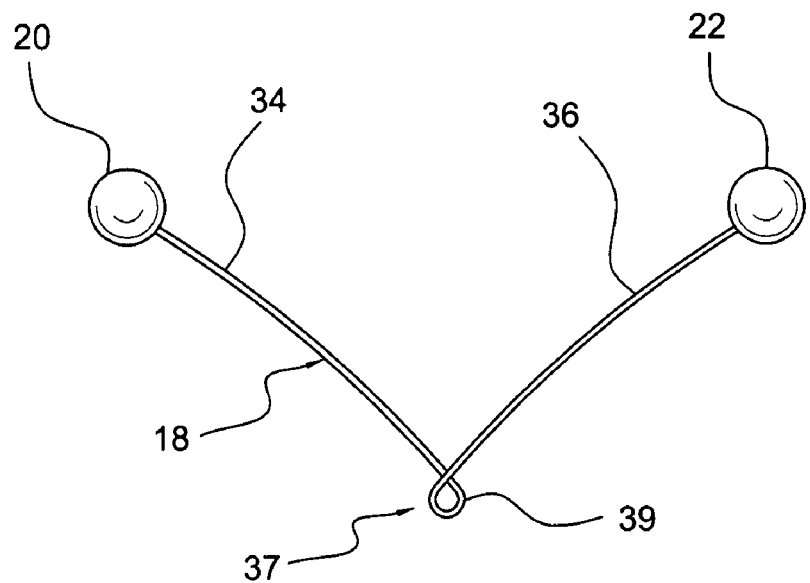
FIGS. 18 and 19 show alternate embodiments of a connection member in accordance with the present invention.
Figure 19:
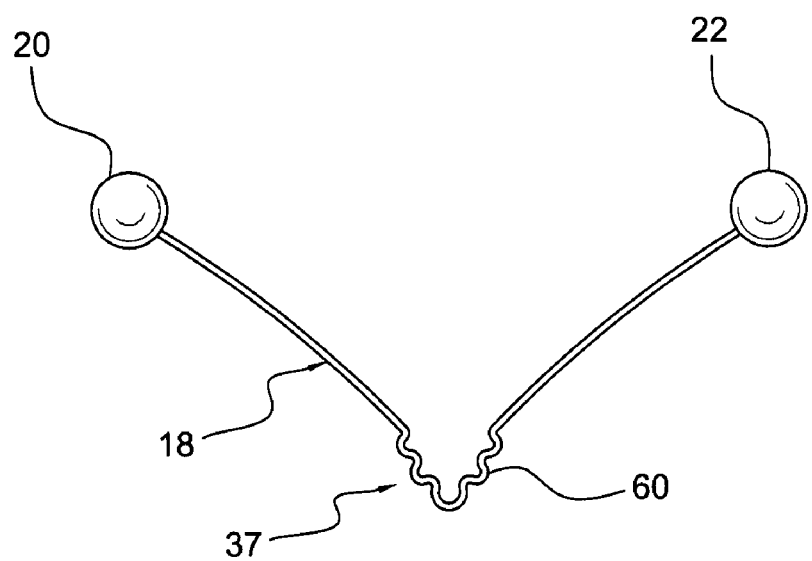

In addition, the spring bias may be imparted to the first leg 34 and the second leg 36 by constructing the connection member 37 with a spring biased loop 39 as shown in FIG. 18 or the spring bias may be controlled by incorporating bends 60 in the connection member 37 as shown in FIG. 19.

Considering the various shapes that may be employed in accordance with a preferred embodiment of the present invention, it is contemplated the outward bias of the first and second legs may be achieved by creating resilience along the length of the first and second legs rather than at the connection point of the first and second legs. For example, where the first and second legs are formed of Nitinol, the first and second legs may be formed such that they bow outwardly when exposed to elevated activation temperature upon placement within the body.

With regard to the material construction of the elongated member 28, and further to the earlier disclosure, it is preferably composed of resilient, biocompatible materials (metal, polymer or composite) or shape memory or superelastic materials (for example, Nitinol), other alloys, or combinations thereof, capable of offering the biasing characteristics discussed herein and required for proper operation of the present invention. If a material desired for use is not biocompatible, it could be covered by another biocompatible material, for example, a coating or a thin-walled plastic tube.

Figure 20:
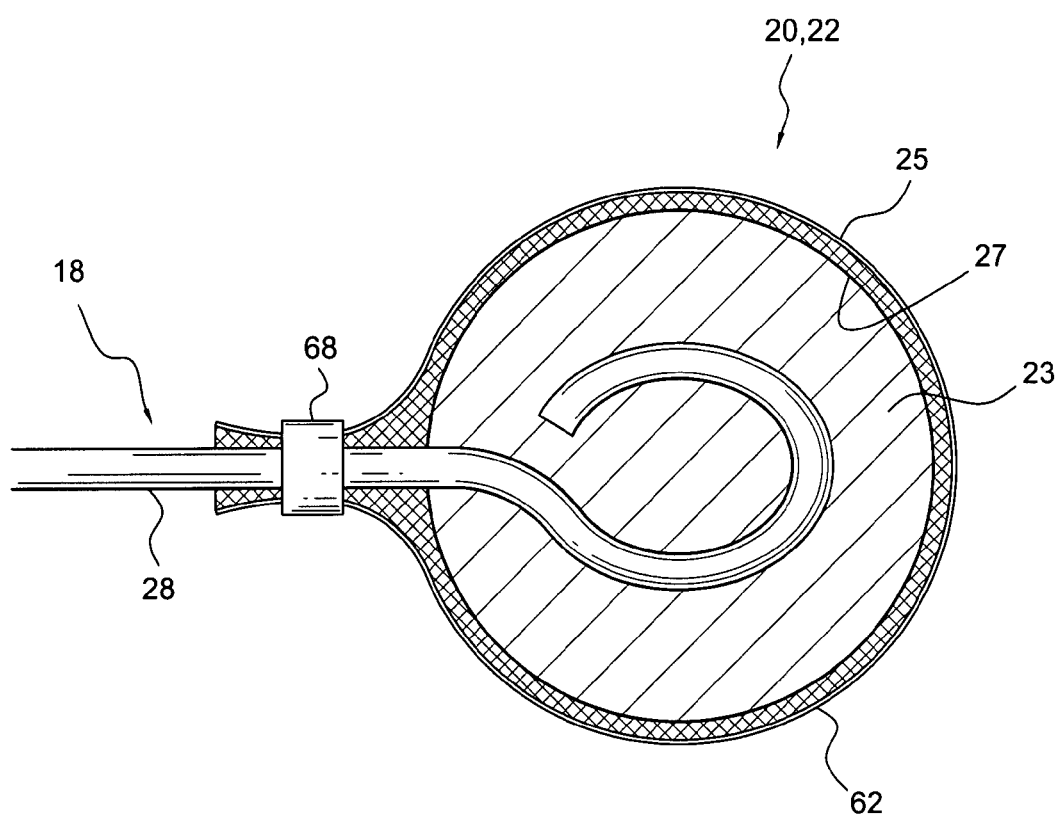
FIG. 20 is a cross sectional view of an orifice plug in accordance with a preferred embodiment of the present invention.

As shown with reference to FIGS. 3-6, 7A-D and 8-11, and in accordance with a preferred embodiment, the orifice plugs 20, 22 are spherical. In accordance with a preferred embodiment, the orifice plug body 23 of the orifice plug 20, 22 is made of silicone. However, depending upon whether it is desired to provide a retrievable orifice plug 20, 22 or a permanently anchored orifice plug 20, 22 the outer surface 25 of the orifice plug 20, 22 will either be the silicone from which it is made (in which case the orifice plug body 23 forms substantially all of the orifice plug 20, 22 as shown in FIGS. 3-6, 7A-D and 8-11) or be composed of a tissue in-growth member 62 which is secured about the outer surface 27 of the silicone orifice plug body (or substrate) 23 (see FIG. 20 which is discussed below in greater detail).

Where a permanent anchoring of the orifice plug 20 within the fallopian tube is desired, and with reference to FIG. 20, a tissue in-growth member 62 is positioned over the silicone substrate material making up the orifice plug body 23 so as to provide the orifice plug 20, 22 with an outer tissue in-growth surface 27. Although reference numeral 20 is used in describing the orifice plug, it will be understood the first and second orifice plugs 20, 22 are identical. The tissue in-growth member 62 is constructed of a material promoting and maintaining tissue in-growth for the purpose of anchoring the orifice plug 20 and creating a seal. It is contemplated the tissue in-growth member 62 could be a biocompatible fabric (for example, a polyester fabric), textile, felt or membrane known by those skilled in the art to encourage tissue in-growth. In accordance with a preferred embodiment of the present invention, it is contemplated the tissue in-growth member 62 may be a knitted polymer textile with appropriate tissue in-growth properties to be considered an acceptable option for use in conjunction with the present invention. The tissue in-growth member could further be covered with a specialty coating that enhances and/or accelerates tissue in-growth.

The tissue in-growth member 62, which is also referred to as a "fabric sock" in accordance with the embodiments described below, may be secured to the orifice plug body 23 through the implementation of various techniques. For example, and with reference to FIG. 21, a cylindrical fabric sock 62 with open ends is placed over the orifice plug body 23 and the fabric sock 62 is twisted so as to create a reduced diameter twisted section 64 distal of the orifice plug body 23. Thereafter, the distal portion 66 of the fabric sock 62 is pulled proximally and over the reduced diameter twisted section 64 and the orifice plug body 23. A band 68 is then applied to the fabric sock 62 proximally of the orifice plug body 23 to secure it in position about the orifice plug body 23.

Figures 21, 22:
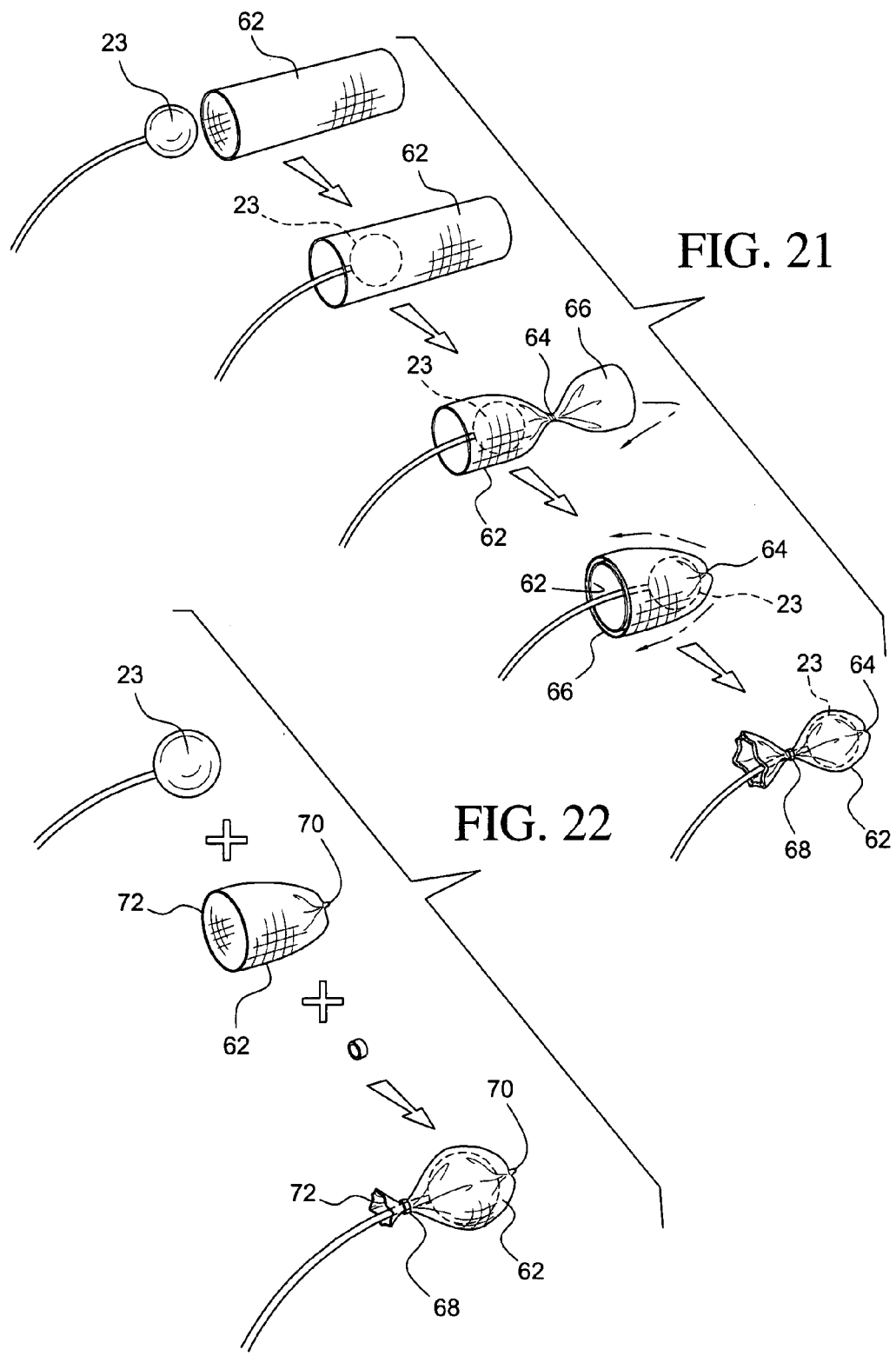

In accordance with an alternate embodiment, and with reference to FIG. 22, a fabric sock 62 with a closed distal end 70 is pulled over the orifice plug body 23. The closed distal end 70 is preferably formed through the application of heat to close the distal end 70 of the fabric sock 62. Once the fabric sock 62 is pulled over the orifice plug body 23 with the closed distal end 70 of the fabric sock 62 covering the distal end of the orifice plug body 23, the proximal end 72 of the fabric sock 62 is closed via the application of a band 68 proximally of the orifice plug body 23 to secure it in position about the orifice plug body 23.

In accordance with yet another embodiment, and with reference to FIG. 23, a cylindrical fabric sock 62 with open ends may be formed in to a double layered, closed ended fabric sock 62 by tying the center 74 of the cylindrical fabric sock 62 and pulling one end 76 thereof over the other end 78 resulting in a fabric sock 62 with a closed distal end 70. Thereafter, the fabric sock 62 is pulled over the orifice plug body 23 with the closed distal end 70 of the fabric sock 62 covering the distal end of the orifice plug body 23, the proximal end of the fabric sock 62 is closed via the application of a band 68 proximally of the orifice plug body 23 to secure it in position about the orifice plug body 23. The embodiment disclosed above with reference to FIG. 24 may be varied by utilizing a washer 80 to constrict the center of the cylindrical fabric sock 62 as opposed to the tie disclosed above.

Figure 25:
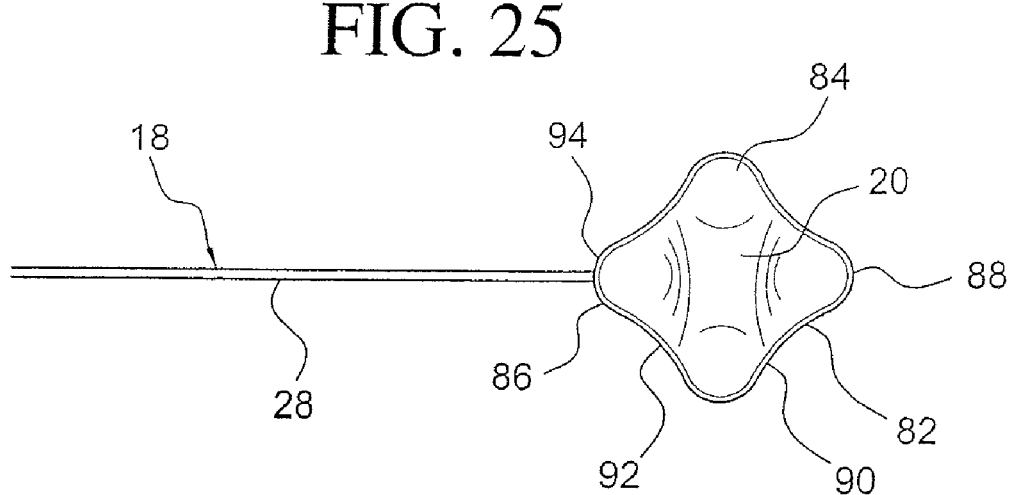
FIGS. 25 and 26 are top plan views showing alternate orifice plug shapes in accordance with the present invention.

Although a spherical orifice plug is disclosed above in accordance with a preferred embodiment, those skilled in the art will appreciate other shapes may be used without departing from the spirit of the present invention. Although reference numeral 20 is used in describing the orifice plug, it will be understood the first and second orifice plugs 20, 22 are identical. In accordance with a first alternate embodiment, and with reference to FIG. 25, the orifice plug 20 takes the form of a "flying saucer". As such, the orifice plug 20 includes an upper conical surface 82 with a domed tip, a central portion 84, and a lower conical surface 86 with a domed tip. More particularly, the upper conical surface 82 is substantially cone-shaped with a concave wall and extends from a rounded crown section 88 to a wider base section 90 which transitions into the central portion 84. The central portion 84 is substantially circular in cross section with a convex wall and extends from a smaller top radius portion to a large central radius portion and back to a smaller bottom radius portion. Beneath the central portion 84 is the lower conical surface 86 that is a mirror image of the upper conical surface 82 and, therefore, extends from a relatively large radius base section 92 to a rounded crown section 94 at its lowest extent.

Figure 26:
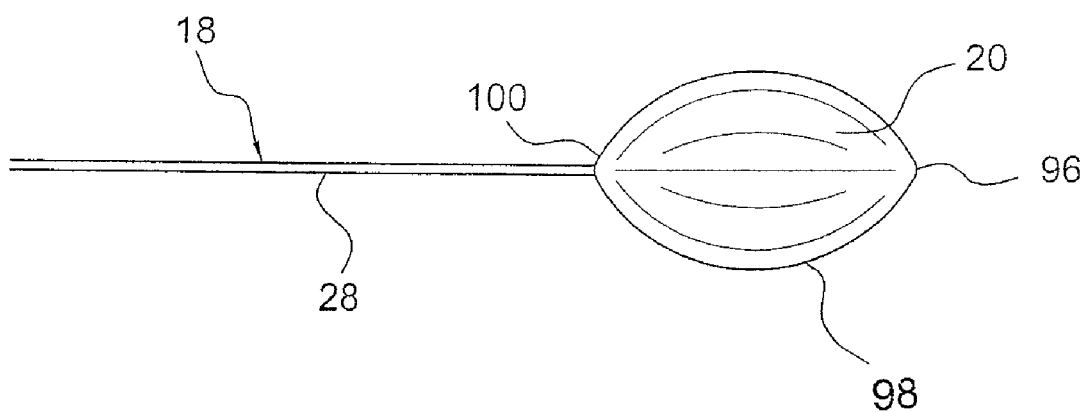

Referring to FIG. 26, an orifice plug 20 with a football shape is disclosed. This shape includes a convex outer wall and a circular cross section when viewed in a plane perpendicular to the longitudinal axis of the orifice plug 20 that goes from a relatively small radius first tip member 96 to a large radius central section 98 and back to a small radius second tip member 100.

Figure 27A:
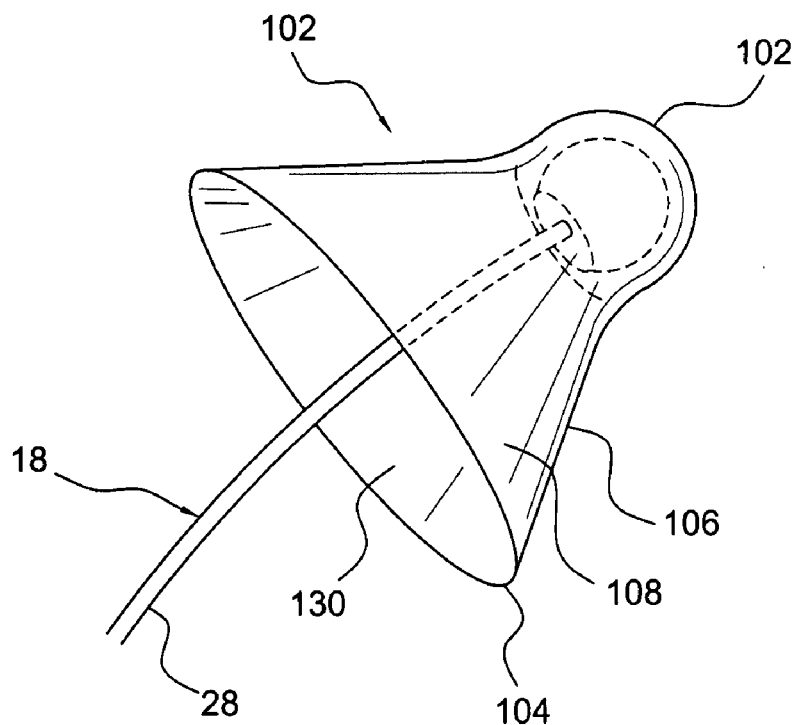
FIGS. 27A and 27B respectively show a perspective view of an alternate shape for an orifice plug and a side schematic view of the same orifice plug positioned within the fallopian tube.
Figure 27B:
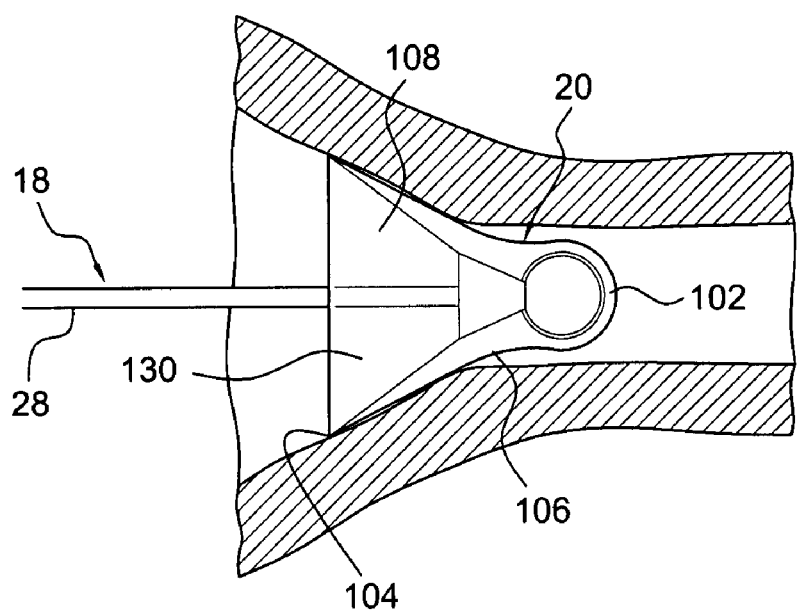

Referring to FIGS. 27A and 27B, a bell-shaped orifice plug 20 may be employed. The bell-shaped orifice plug 20 includes a rounded crown section 102 which extends outwardly as it moves from the tip toward the rim 104 of the bell to create a substantially straight or concave outer surface 106 along the sidewalls 108 of the orifice plug 20. In accordance with a preferred embodiment, the rounded crown section 102 is substantially solid and the portion of the orifice plug 20 along the sidewalls 108 is hollow (defining a cavity 130 along the underside of the orifice plug 20) adding flexibility to the sidewalls 108 as they extend to the rim 104 of the bell.

Figure 28:
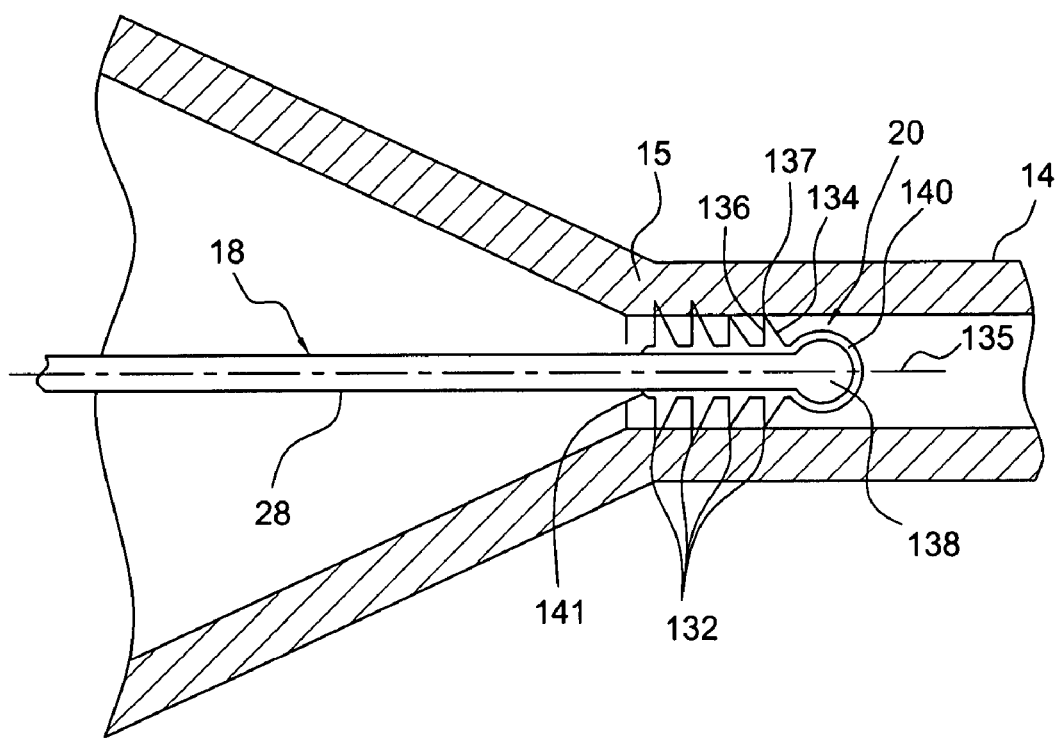
FIGS. 28, 29, 30, 31A, 31B and 31C are schematics of alternate embodiments of orifice plugs that may be used in accordance with the present invention.

With reference to FIG. 28, the orifice plug 20 may also be formed with multiple tapered ring members 132. Each of the ring members 132 includes a forward facing surface 134 and a rearward facing surface 136. The forward facing surface 134 is angled for creating an acute angle relative to the fallopian tube 14 into which it is inserted (that is, the forward facing surface 134 tapers proximally as it extends from the central longitudinal axis 135 of the orifice plug 20 toward the free end 137 thereof) to facilitate insertion while the rearward facing surface 136 is oriented to create a substantially perpendicular angle relative to the fallopian tube 14 to hinder removal from the fallopian tube 14 after insertion. The ring members 132 each form a seal that engages the wall of the fallopian tube 14 creating a barrier thereof. A rounded ball member 138 is formed at the distal end 140 of the orifice plug 20. The addition of the round ball member 138 helps in reducing trauma to the tissue as the orifice plug 20 is inserted within fallopian tube 14.

The multiple ring members 132 increase the likelihood of creating a complete barrier. The material from which the ring members 132 are manufactured could be hard or soft and the successive radii of the ring members 132 preferably increase in diameter over an appropriate length as the orifice plug 20 extends from its distal end 140 toward its proximal end 141. As a result, the orifice plug 20 would seal repetitively starting within the fallopian tube 14 and progressing out past the ostium 15.

Figure 29:
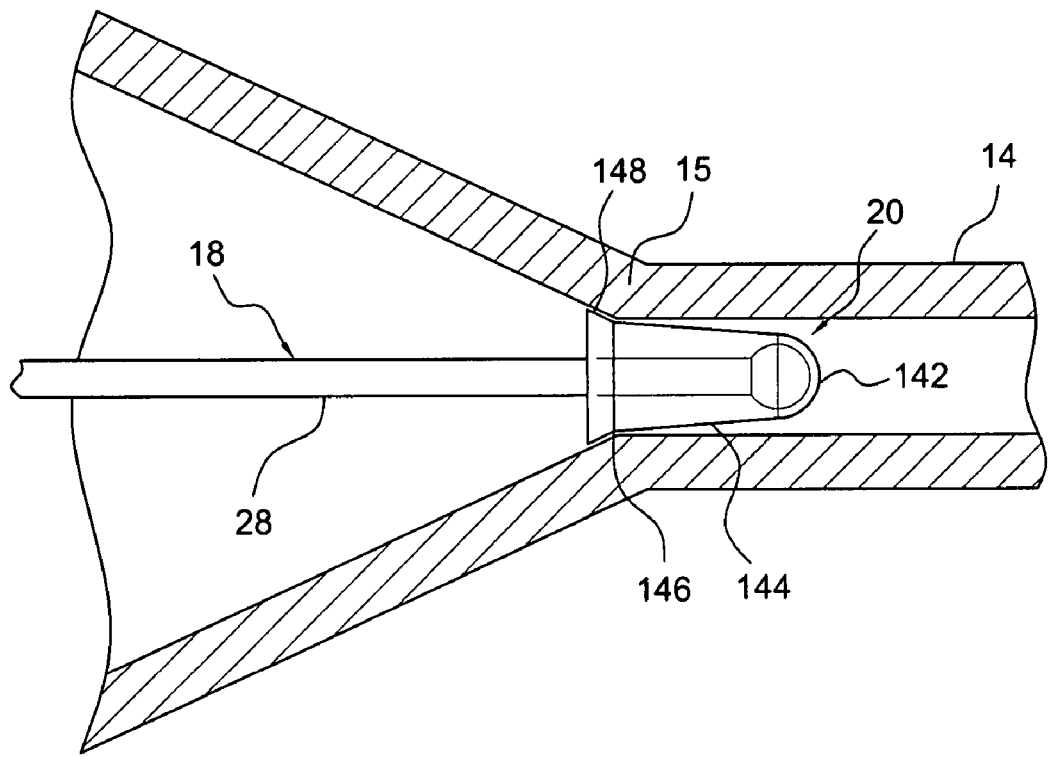

Referring to FIG. 29, yet a further embodiment of an orifice plug 20 is disclosed. This orifice plug 20 includes a rounded tip 142 and an outwardly tapering wall 144. At the proximal end 146 of the outwardly tapering wall 144 is formed a thin pliable flange 148. The flange 148 functions as both the edge of the orifice plug 20 and a face for sealing the fallopian tube 14 at the ostium 15 from the external environment.

Figure 30:
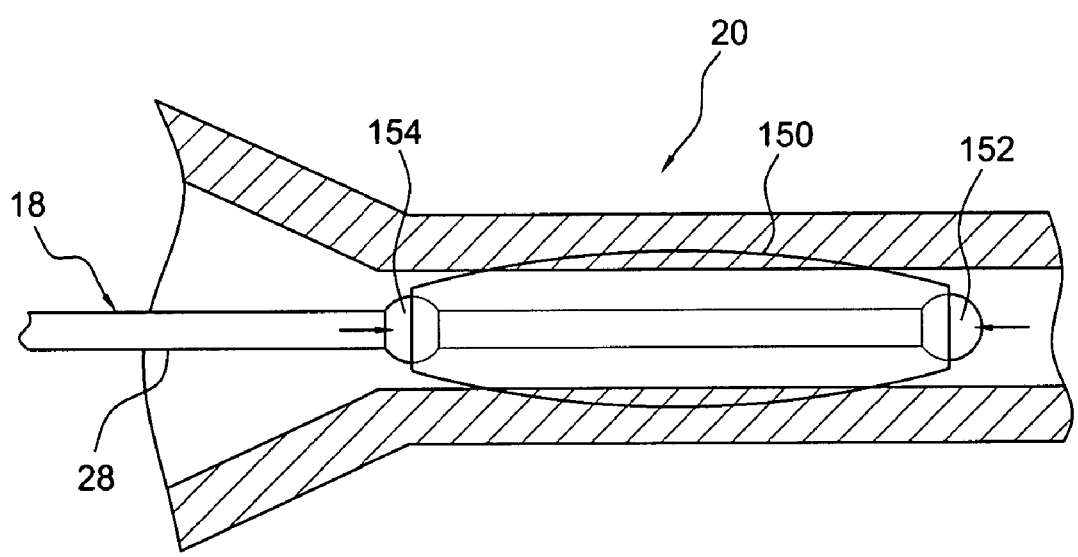

Yet a further embodiment is disclosed with reference to FIG. 30. This embodiment includes an orifice plug 20 with a prolate spheroid shape, that is, a sphere elongated in the direction of a line joining the poles of the sphere (in this case the longitudinal axis of the orifice plug 20). The shape is achieved by securing a tube-like member 150 in a compression state between first and second constraining members 152, 154 at the respective distal and proximal ends of the orifice plug 20. In accordance with a preferred embodiment of this design, the tube-like member 150 is secured to pliable balls, that is, the constraining members 152, 154 at the respective distal and proximal ends of the orifice plug 20.

Figure 31A:
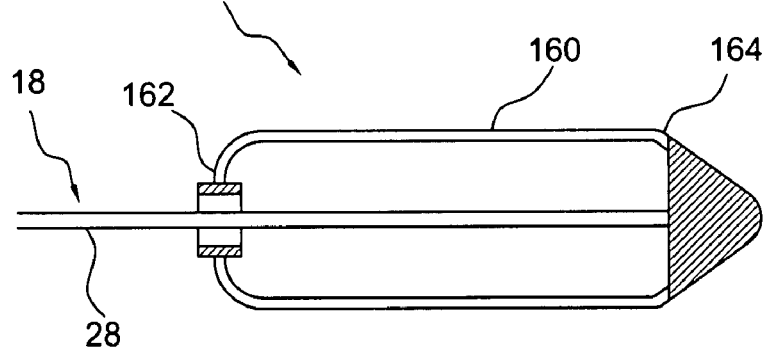
Figure 31B:
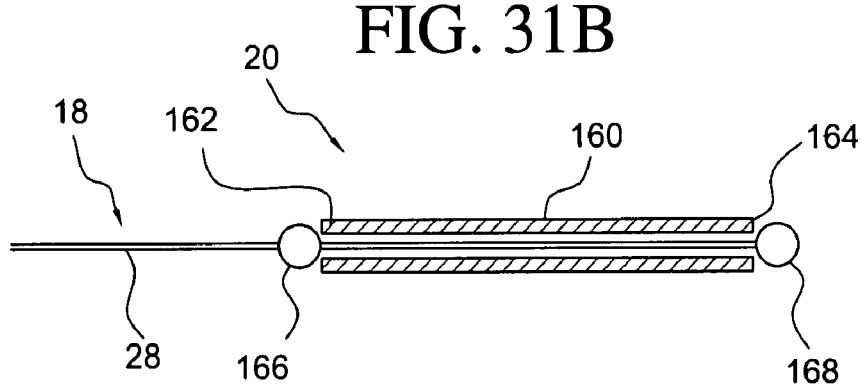
Figure 31C:
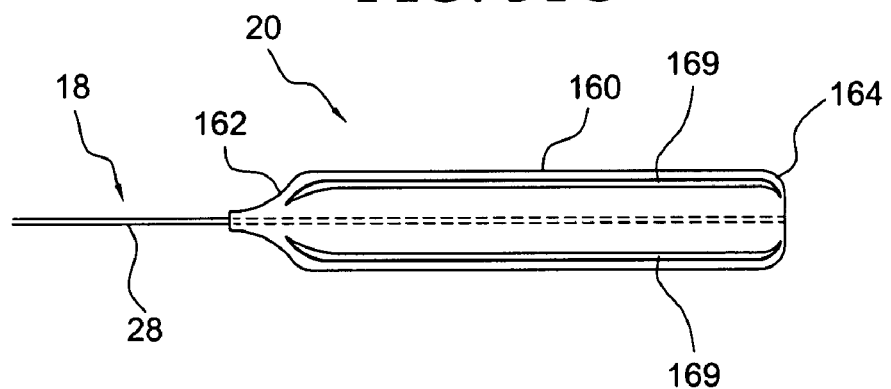

Referring to FIGS. 31A, 31B and 31C, the orifice plug 20 may be designed with a self-adjusting configuration whereby the diameter thereof extends outwardly upon insertion within the fallopian tube. In accordance with each of these embodiments, a biocompatible polymeric, tube-like member 160 spans the length of the orifice plug 20 and is restrained in a manner allowing expansion or contraction thereof such that the diameter of the tube-like member 160 selectively increases as the proximal end 162 and distal end 164 thereof are moved toward and away from each other (see FIGS. 31A and 31B) or as the tube-like member 160 expands (see FIG. 31C). With regard to the embodiment shown in FIG. 31A, the tube-like member 160 is made from a material which contracts upon positioning within the fallopian tube. This will cause the proximal end 162 of the tube-like member 160, which is coupled to the elongated member 28 for movement relative to the elongated member 28, to move toward the distal end 164 of the tube-like member 160 and result in an increase in the diameter of the tube-like member 160. As to the embodiment shown in FIG. 31B, the proximal end 162 and the distal end 164 of the tube-like member 160 are restrained by respective first and second abutment members 166, 168 formed along the elongated member 28. In at least this region, the elongated member 28 is made of a shape memory material, for example, Nitinol, and the distance between the first and second abutment members 166, 168 decreases upon the placement of the orifice plug 20 within the fallopian tube. This will cause the proximal end 162 of the tube-like member 160 to move toward the distal end 164 of the tube-like member 160 and result in an increase in the diameter of the tube-like member 160. As to the embodiment shown with reference to FIG. 31C, the tube-like member 160 is provided with elongated slots 169 allowing for expansion of the tube-like member 160 when it is placed within the fallopian tube. The tube-like member 160 is made from a material which expands upon positioning within the fallopian tube. This will cause outward expansion of the tube-like member 160 since the distal end 164 and proximal end 162 of the tube-like member 160 are fixedly coupled to the elongated member 28.

Figure 32A:
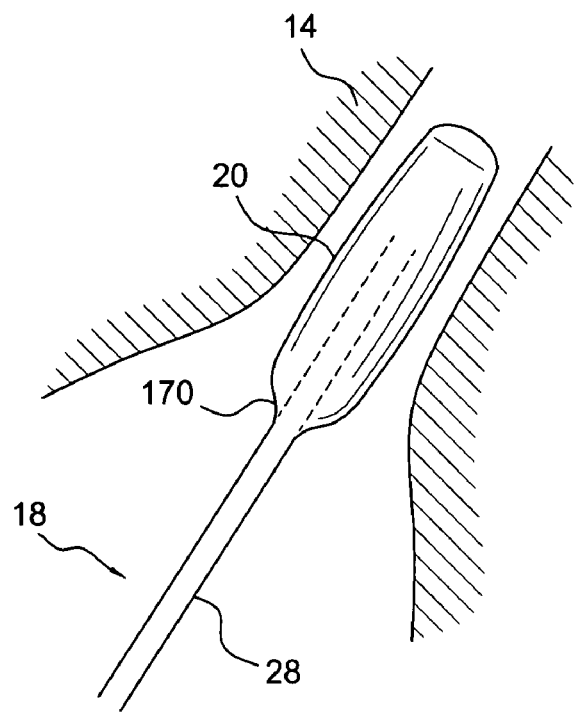
FIGS. 32A and 32B are side schematic views of an alternate orifice plug in accordance with the present invention before and after expansion thereof within the fallopian tube.
Figure 32B:
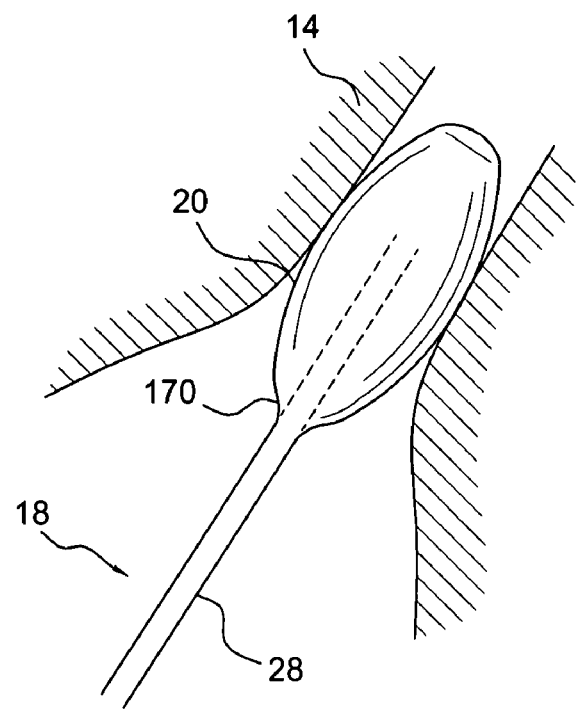

Once again, and referring to FIGS. 32A and 32B, an expanding orifice plug 20 is disclosed. The orifice plug 20 is manufactured from an elastic material which expands upon placement in the fallopian tube 14. Swelling may be achieved by means of applying a temporary tension to the proximal portion 170 the elastic orifice plug 20 and then is either released based upon positioning of the orifice plug 20 relative to a predetermined anatomical structure or released over a time delay. In addition, the orifice plug 20 could be manufactured from a hydrophilic substance that swells during insertion so as to alter its shape. By allowing the orifice plug 20 to swell inside the fallopian tube 14, the lumen is occluded. In addition, the orifice plug 20 could be positioned within the uterine cavity sealing on the ostia and a smaller plug once past the cervical limitations swells to the desired and shape. In accordance with a preferred embodiment of the present invention, the swelling material could be comprised of a single compound or a combination of compounds yielding different properties, such as, durability and conformance, thereby producing a superior seal. A hydrogel polymeric compound is considered an appropriate material for this purpose at it relies on the ambient moisture of the physiology to cause the swelling activation.

Figure 33:
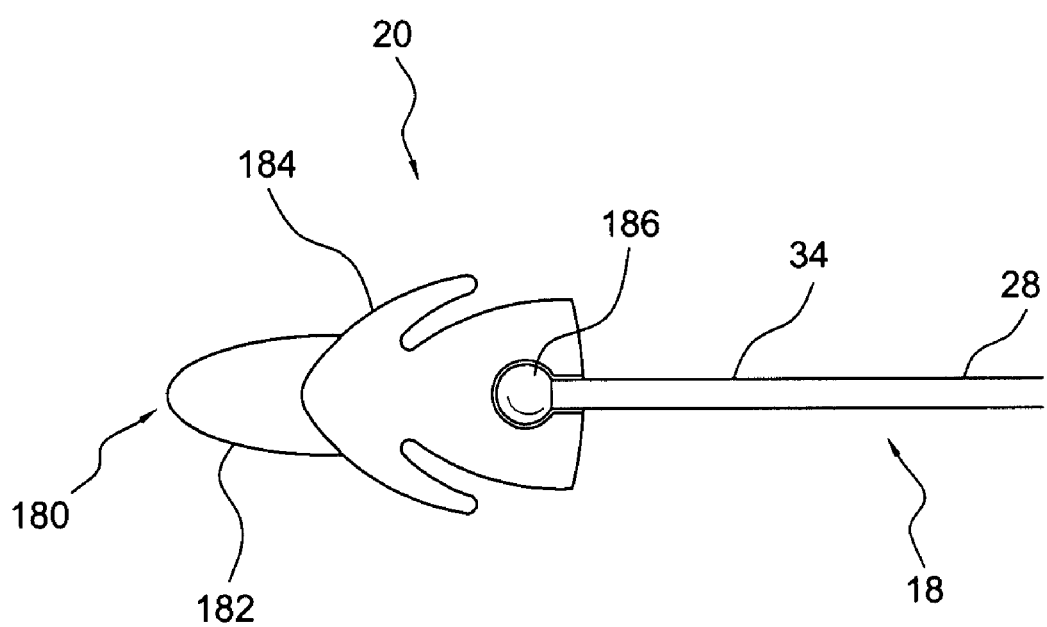
FIGS. 33, 34, 35, 36, 37 and 38 are schematic views of alternate embodiments of an orifice plug in accordance with the present invention.

Further, and with reference to FIG. 33, a ball and socket arrangement for an orifice plug 20 is disclosed. In accordance with such an embodiment, the orifice plug 20 is designed with a leading end 180 having a guiding nose 182 shaped and dimensioned to find the fallopian tube and align therewith. Once the fallopian tube is found, an elastomeric plug member 184 is forced within the fallopian tube. Articulation of the orifice plug 20 is achieved by coupling the plug member 184 to the first (and second) leg 34 via a ball joint 186. The ball and socket joint of this embodiment would provide the orifice plug with a degree of freedom to swivel and angularly align with the ostium creating a more even distribution of sealing force and area.

Figure 34:
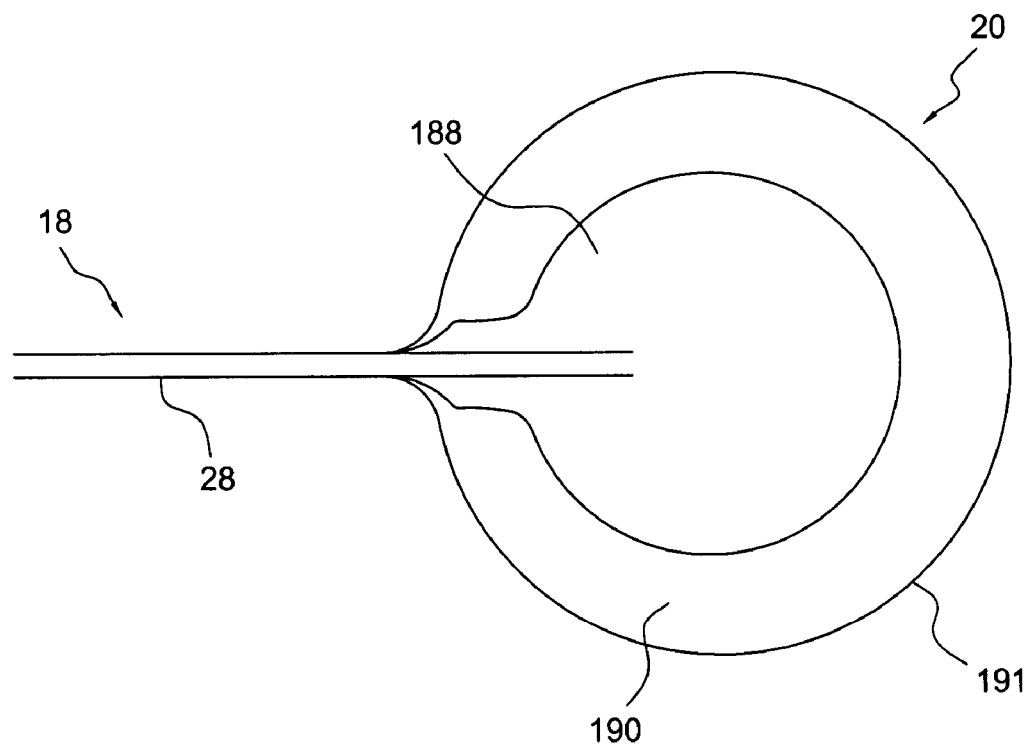

As discussed above, the orifice plugs are composed of silicone in accordance with a preferred embodiment. However, and for each of the orifice plug shapes disclosed above, the orifice plug may be formed in a dual density configuration of various biocompatible elastomers. In particular, and with reference to FIG. 34, the inner portion 188 of the orifice plug 20 is made from a relatively hard material and forms a foundation for the orifice plug 20. Affixed over the inner portion 188 is an outer soft pliable material 190. The soft pliable material 190 forms the outer surface 191 of the orifice plug 20 and is believed to form a better seal at the entrance of the fallopian tube based upon its conforming nature.

Figure 35:
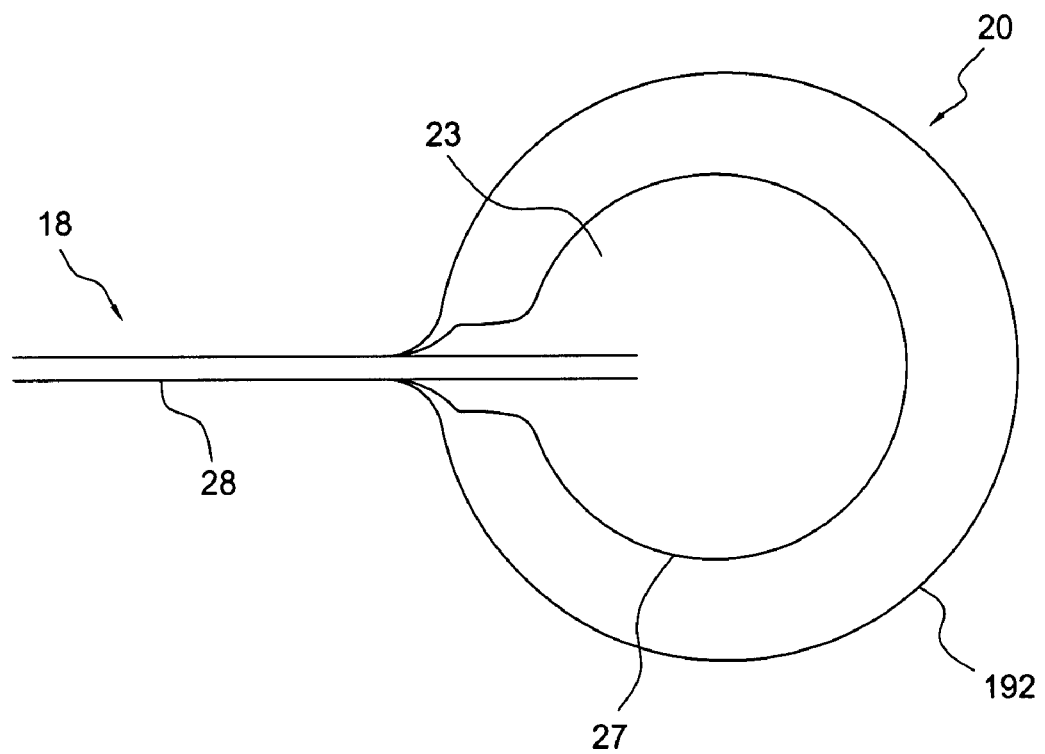

In accordance with an alternate embodiment, and with reference to FIG. 35, the orifice plug 20 maybe formed with a hard outer shell 192 (for example, like gelatin tablet material) temporarily affixed to the outer surface 27 of the main orifice plug body 23 of the orifice plug 20 that is made of a soft pliable material (or a dual density configuration as described above) for the purpose of protecting the softer inner material. The hard outer shell 192 behaves like a slippery surface during insertion and deployment. However, the hard outer shell 192 is composed of a bioabsorbable material which quickly dissolves upon deployment within the fallopian tube. As a result, the hard outer shell 192 dissolves and is discharged or absorbed allowing the soft pliable material of the outer surface 27 to ultimately seat occluding the fallopian tube.

Figure 36:
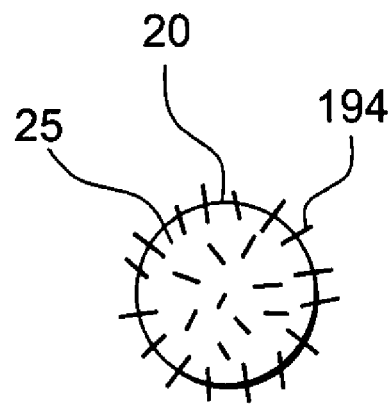
Figure 37:
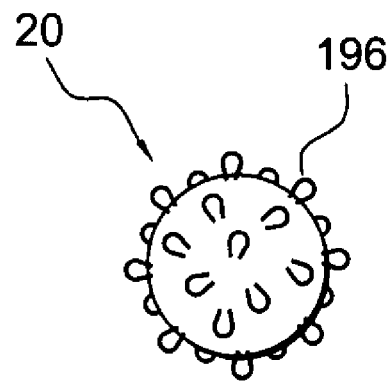

As discussed above in accordance with a preferred embodiment, enhanced coupling of the orifice plug to the tissue surface is achieved by the application of a tissue in-growth member of mesh about the silicone outer surface of the orifice plug. However, it is contemplated other techniques may be employed to achieve desirable coupling of the orifice plug within the fallopian tubes. For example, and in accordance with one embodiment as shown with reference to FIG. 36, the outer surface 25 of the orifice plug 20 is provided with tissue in-growth promoting/compatible whiskers 194. The tissue in-growth promoting/compatible whiskers 194 help to integrate the orifice plug 20 within the anatomy and ensure a substantial seal. Similarly, and with reference to FIG. 37, tissue in-growth promoting/compatible loops 196 may be integrated into the orifice plug 20 for the same purpose of securing the same to the anatomy and creating a seal.

Figure 38:
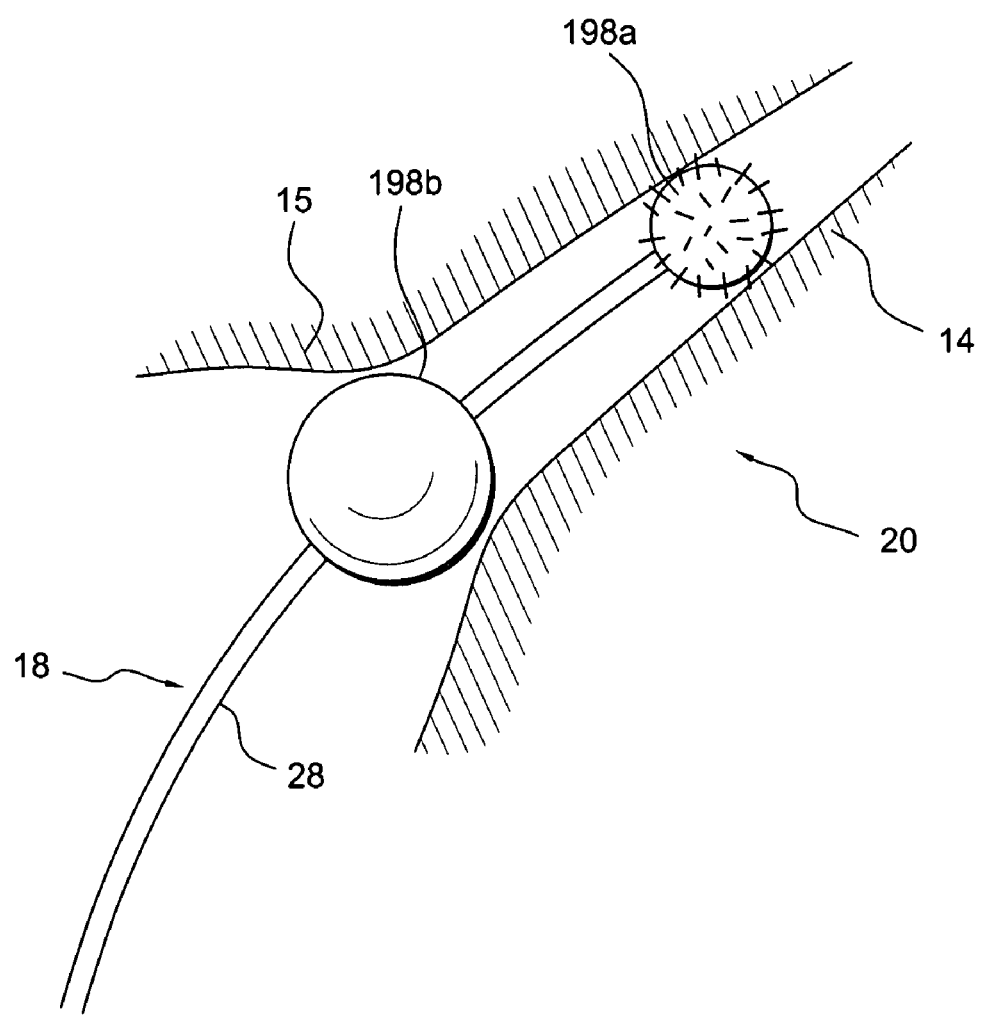

In accordance with yet a further embodiment, and referring to FIG. 38, a series of plug members 198a, 198b may be formed along the length of the first (and second) legs 34. In accordance with such an embodiment it is contemplated the distal most plug member 198a would have a smaller diameter than the more proximal plug member 198b. The smaller plug member 198a would be provided with or without tissue in-growth treatment and would be small enough to pass the ostium 15 and assist in guiding the device into the fallopian tube 14. The larger plug member 198b would be sufficiently sized for guiding to the ostium 15 and sealing thereon. The smaller plug member 198a located in the fallopian tube 14 would help to maintain the larger plug in position.

While various orifice plug shapes are disclosed herein, it is contemplated orifice plug shapes as disclosed in commonly owned PCT Publication No. WO2006/088909, which is based upon International Application No. PCT/US2006/005245, filed Feb. 15, 2006, entitled "INTRAUTERINE FALLOPIAN TUBE OCCLUSION DEVICE AND METHOD FOR USE", which is incorporated herein by reference, may be employed within the spirit of the present invention.

Figure 2:
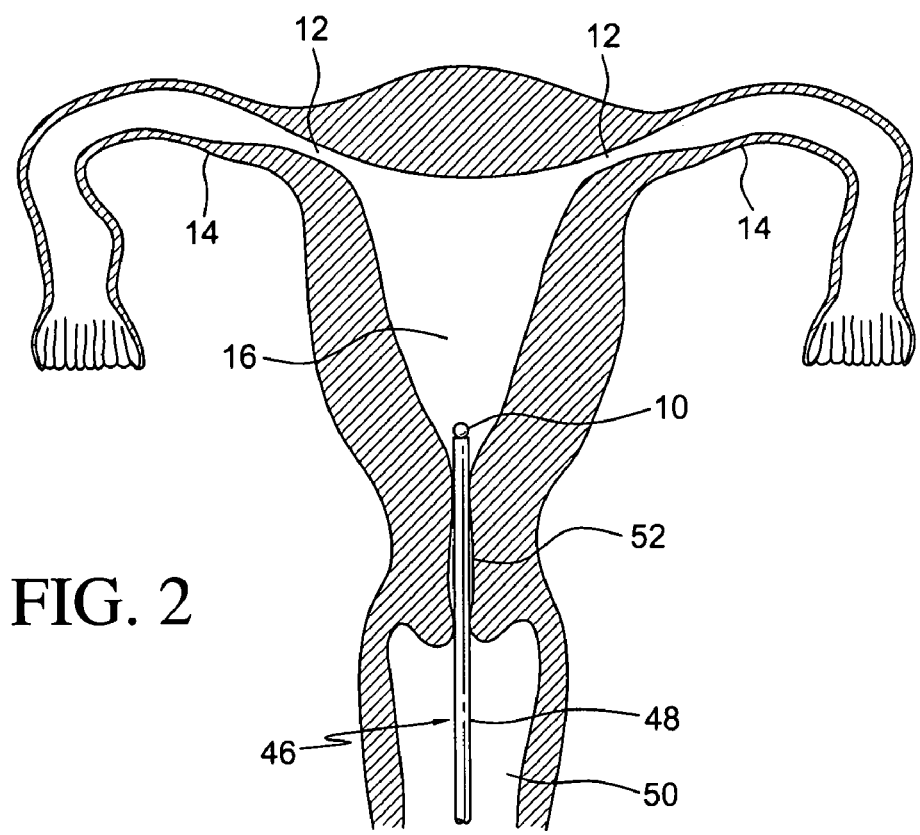
Figure 3:
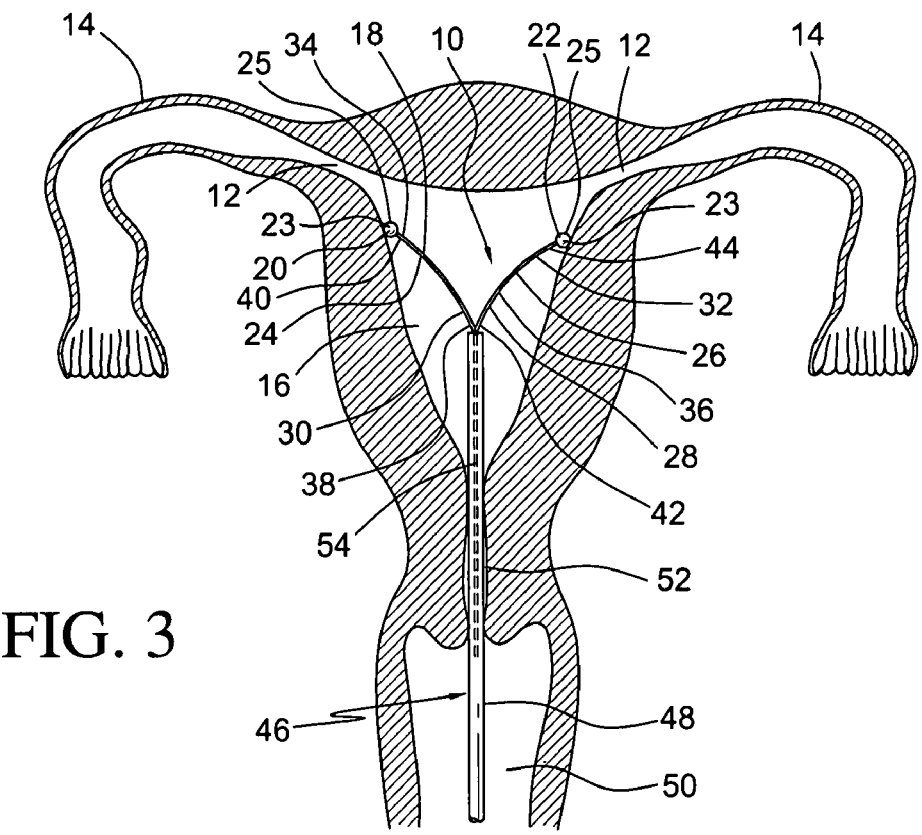
Figure 4:
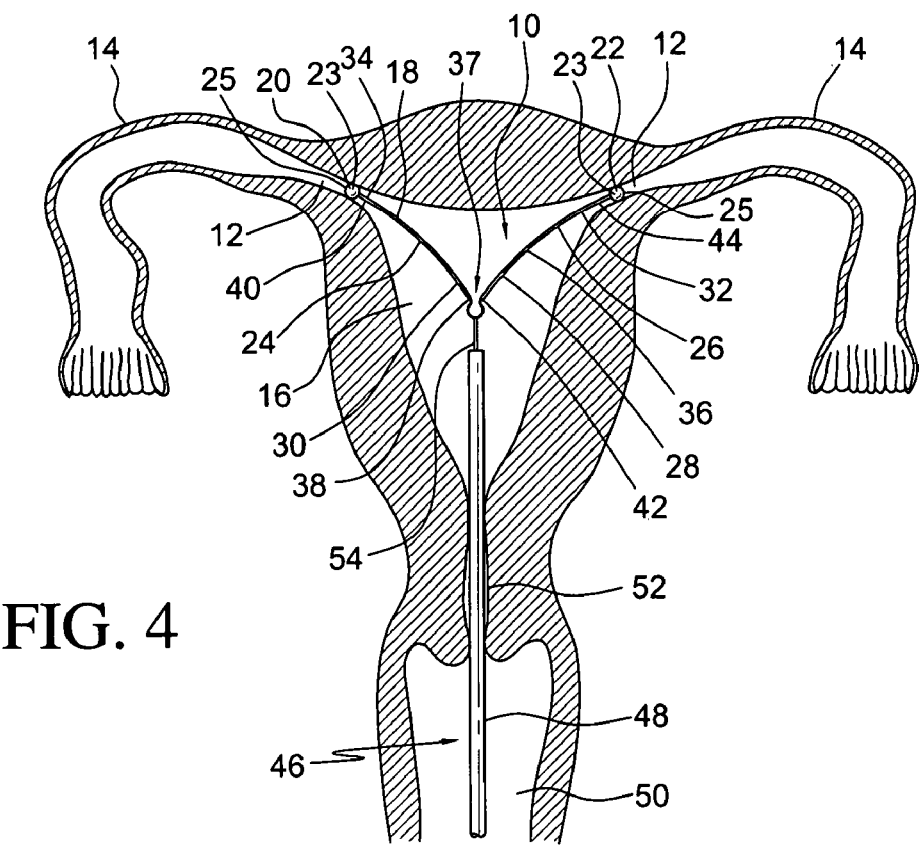
Figure 5:
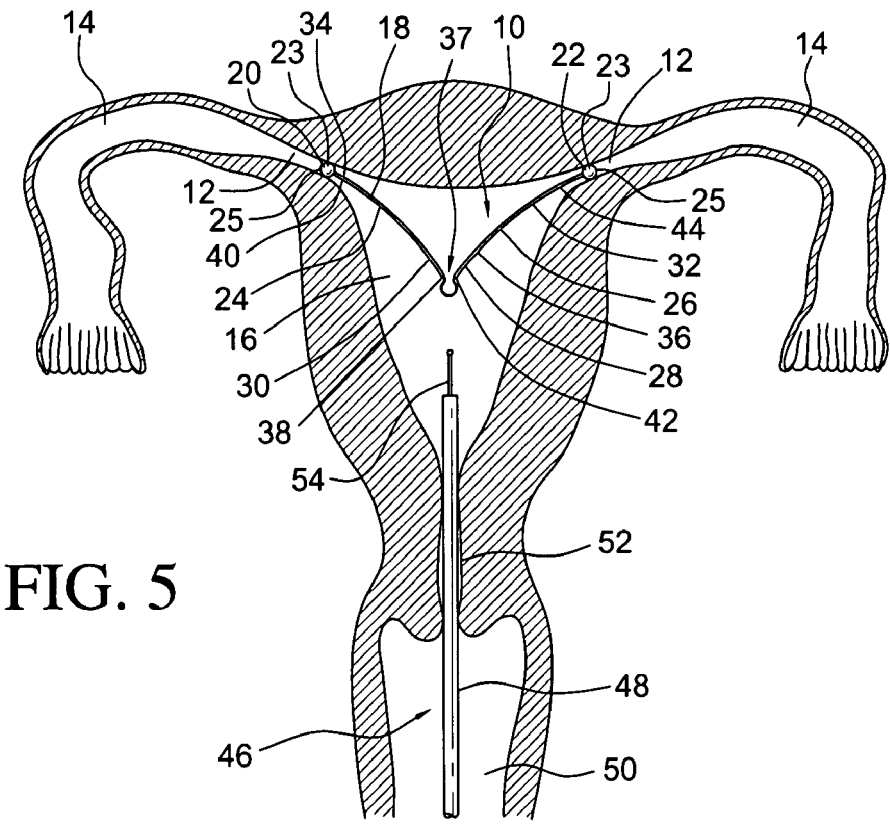
Figure 6:
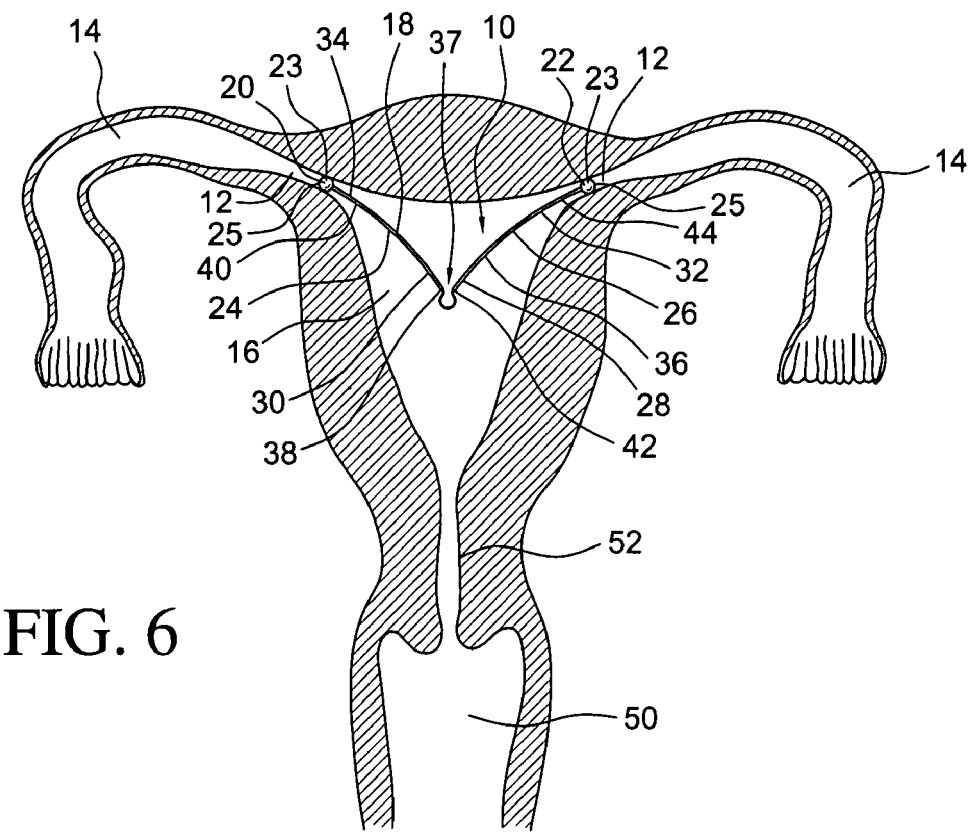

Delivery of the present occlusion device is achieved in the manner described with reference to commonly owned PCT Publication No. WO2006/088909, which is based upon International Application No. PCT/US2006/005245, filed Feb. 15, 2006, entitled "INTRAUTERINE FALLOPIAN TUBE OCCLUSION DEVICE AND METHOD FOR USE", which is incorporated herein by reference. Briefly, and with reference to FIGS. 1 to 6, the occlusion device 10 is packaged in a small caliber longitudinal delivery container 48 which forms part of the delivery apparatus 46. This delivery container 48 is advanced into the uterine cavity 16 through the vagina 50 and cervix 52 (FIG. 2). Once inside the uterine cavity 16, the occlusion device 10 is partially released and advanced from the delivery container 48 via a delivery rod 54 extending through the delivery container 48 for pushing the occlusion device 10 from its storage position within the delivery container 48, preferably, while pulling the delivery container (or sheath) 48 back so as to prevent damage to the uterus or occlusion device 10. This releases the present occlusion device 10 from within the delivery container 48 and allows the occlusion device 10 (with the delivery rod 54 secured thereto) to take a shape of a "Y" (FIG. 3). The occlusion device 10 is further advanced within the uterine cavity 16. As the occlusion device 10 opens with the first and second legs 34, 36 moving apart, the orifice plugs 20, 22 of the occlusion device 10 distally reach the back wall of the uterine cavity 16, and direct themselves to the orifices 12 of the fallopian tubes 14 until they seat at the orifices 12 of the fallopian tubes 14 or within the fallopian tubes 14 (FIG. 4). At that point when the occlusion device 10 can be compressed against the fallopian tube orifices 12 it will be released (FIG. 5), whether manually or automatically, from the delivery apparatus 46. The delivery apparatus 46 will be removed and the present occlusion device 10 will stay in place (FIG. 6).

A proposed embodiment for the delivery apparatus 46 is illustrated in FIGS. 7A to 7D. This illustration shows the delivery apparatus 46 with its orifice plugs 20, 22 arranged longitudinally within the delivery container 48. Because of the need to maintain the delivery container 48 in the lowest profile possible (the bigger the delivery system the more dilatation of the cervix is needed), the orifice plugs 20, 22 are located, staggered, one in front of the other. This also means that the two "legs" 34, 36 of the occlusion device 10 in this embodiment are a slightly different length.

Figure 9:
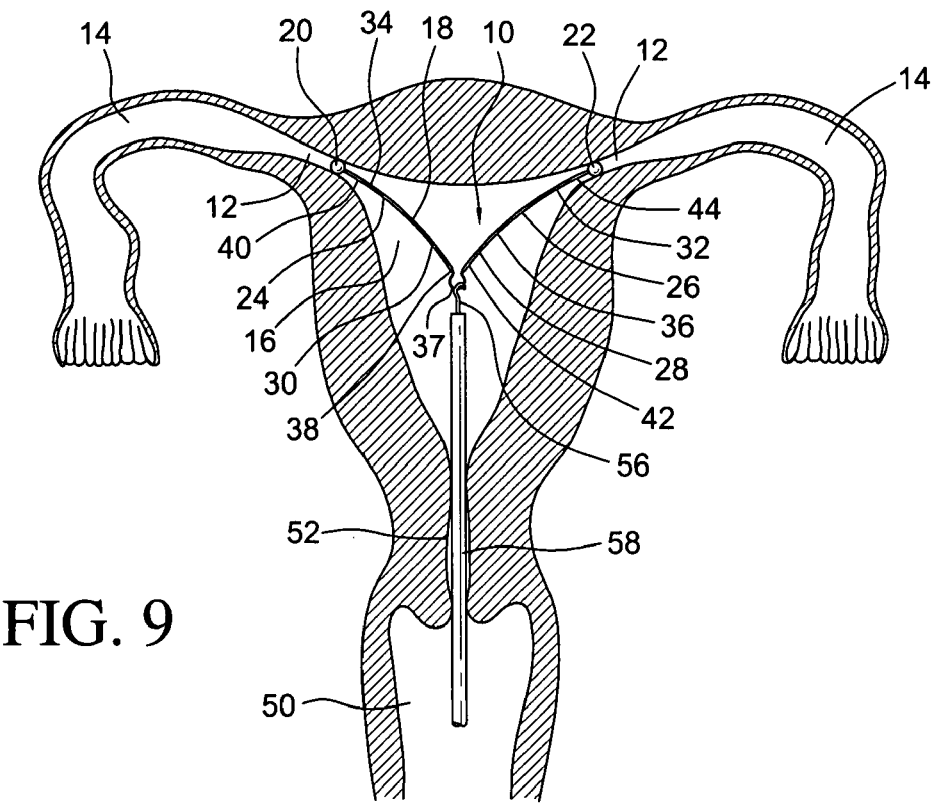
Figure 10:
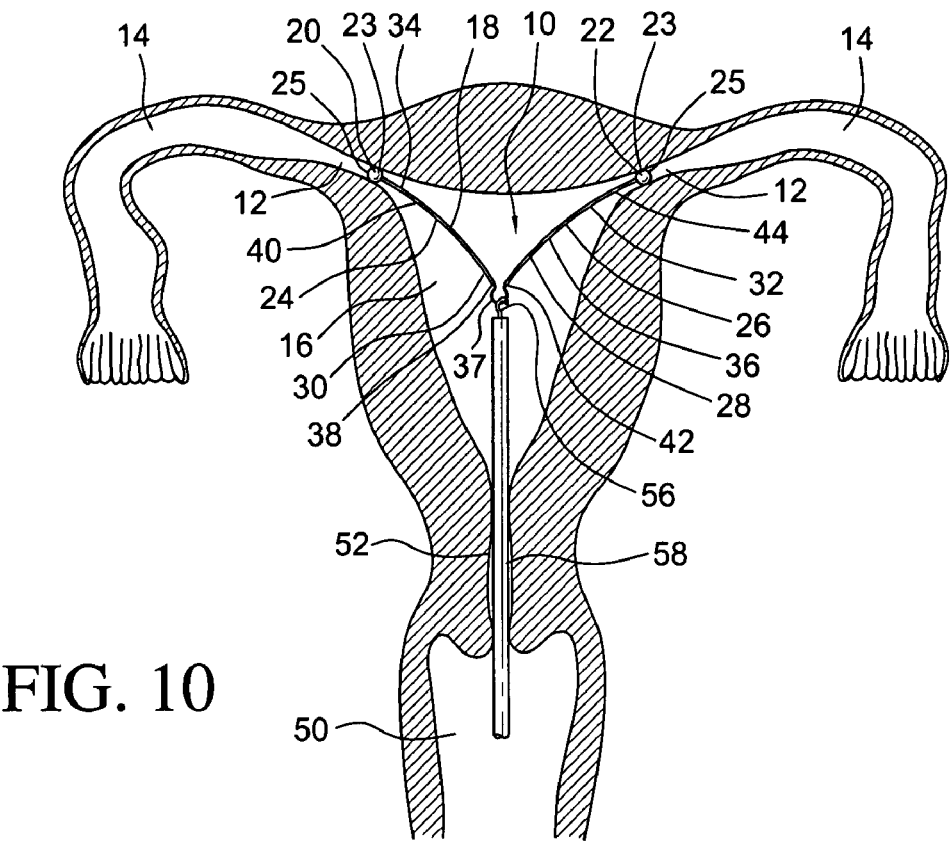
Figure 11:
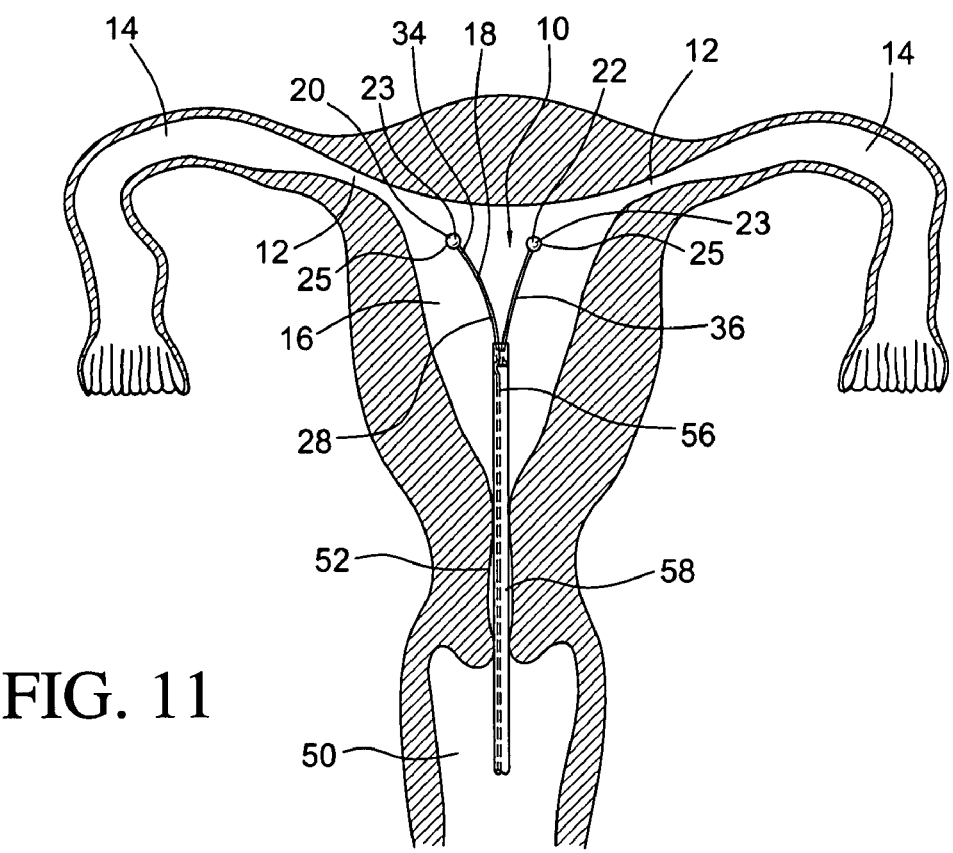
Figure 12:
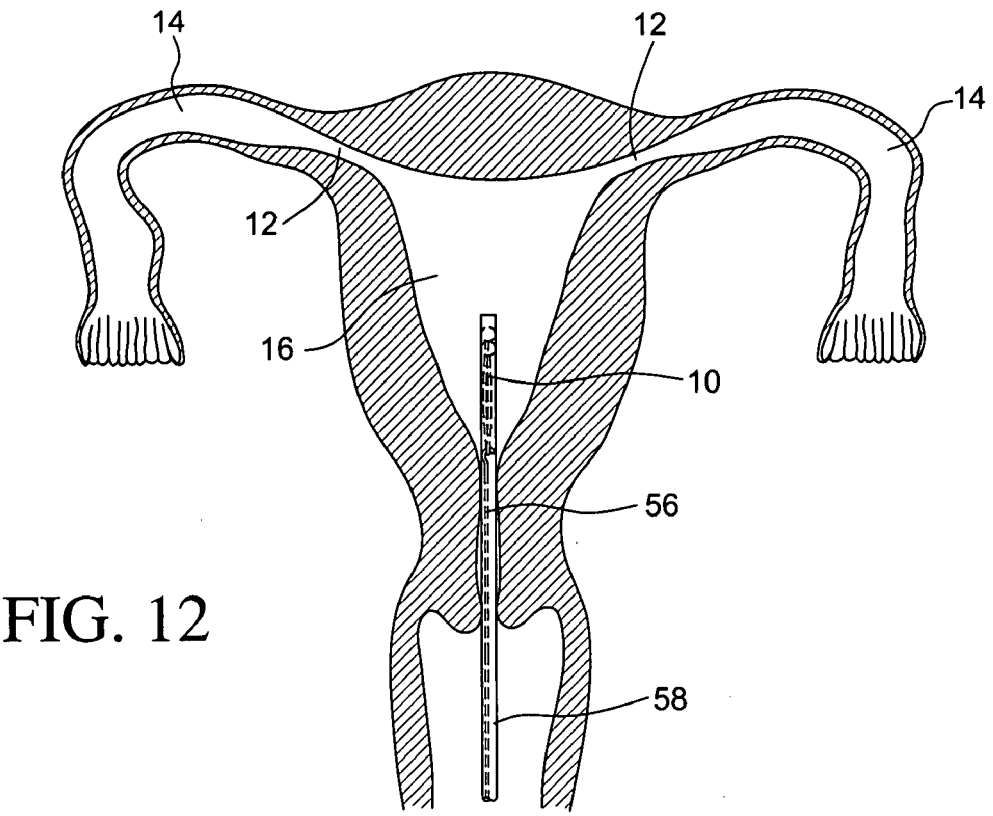
Figure 13:
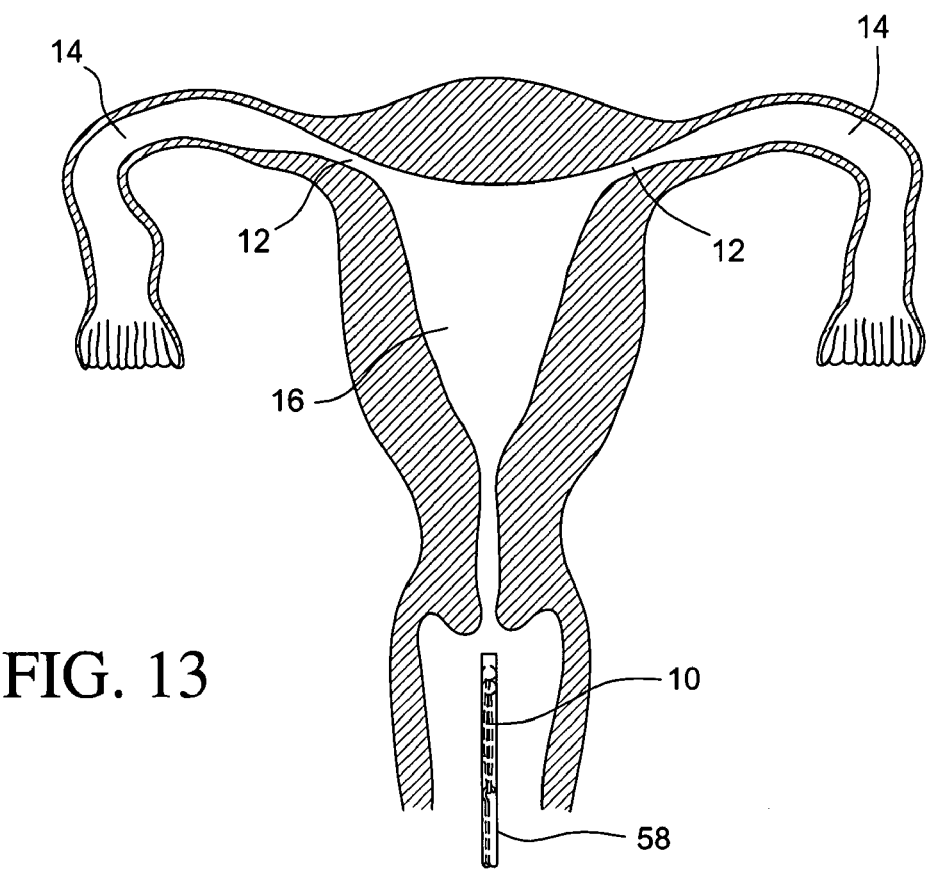

When removal of the occlusion device 10 is desired, a hook 56, or other removal apparatus that engages the occlusion device 10, will be advanced through the vagina 50 and cervix 52 (FIG. 8) and the connection point (for example, a metallic spring) between the orifice plugs 20, 22 and the first and second legs 34, 36 will be grasped (FIG. 9). The hook 56 will pull on the occlusion device 10 and insert it into a sheath 58 or into the hysteroscope (FIGS. 10, 11, 12). At that stage, the contained occlusion device 10 is removed from uterus and out through the cervix 52 and vagina 50 (FIG. 13). This removal would be done either with or without direct visualization or under fluoroscopic guidance.

The novelty of the present device is that, in addition to being an intrauterine device, it will actively occlude the fallopian tubes. This occlusion will prevent sperm or other material from migrating from the uterus to the fallopian tubes and vice versa.

The present device offers a variety of other uses. These uses include applications for contraception, either temporary or permanent; especially for women who do not use IUDs because of the "post fertilization-embryo destruction" mechanism associated with the IUD's birth control. The present occlusion device may also be used by women who do not wish to undergo a tubal ligation surgery.

The present occlusion device may potentially also be used in the treatment of endometriosis. Back flush of menstrual blood through the fallopian tubes is a proposed mechanism for this disease. The present occlusion device will allow occlusion of the fallopian tubes as a possible treatment.

Endometriosis is usually affecting younger patients and other methods of tubal ligation or occlusion are not warranted.

Although a preferred embodiment disclosed above shows the orifice plugs as being permanently coupled to the ends of the resilient body, the resilient body, delivery rod and container may serve as a delivery system of the orifice plugs to the orifices of the fallopian tubes. More particular, and with reference to FIGS. 14, 15 and 16, the concepts underlying the present invention are utilized in conjunction with the shape of the uterine cavity 16 to conform the first and second orifice plugs 120, 122 of the occlusion device 110 in the orifices 12 of the fallopian tubes 14. As with the prior embodiments, the orifice plugs 120, 122 may contain any kind of material or medicine to be delivered into the orifices 12 or the fallopian tubes 14.

The orifice plugs 120, 122 are releasably secured to the first and second ends 124, 126 of the resilient body 118 and, therefore, may be left in place by separating them from the resilient body 118. As those skilled in the art will certainly appreciate a variety of methods for separation of the orifice plugs 120, 122 with the resilient body 118 may be employed within the spirit of the present invention. For example, release may be achieved by mechanically coupling mechanisms or heat activated release mechanism wherein a coupling structure melts or separates the connection or connections between the plugs and the resilient body when the device is placed within the body (either immediately or over time and hence separate the plugs from the delivery device).

Figure 39:
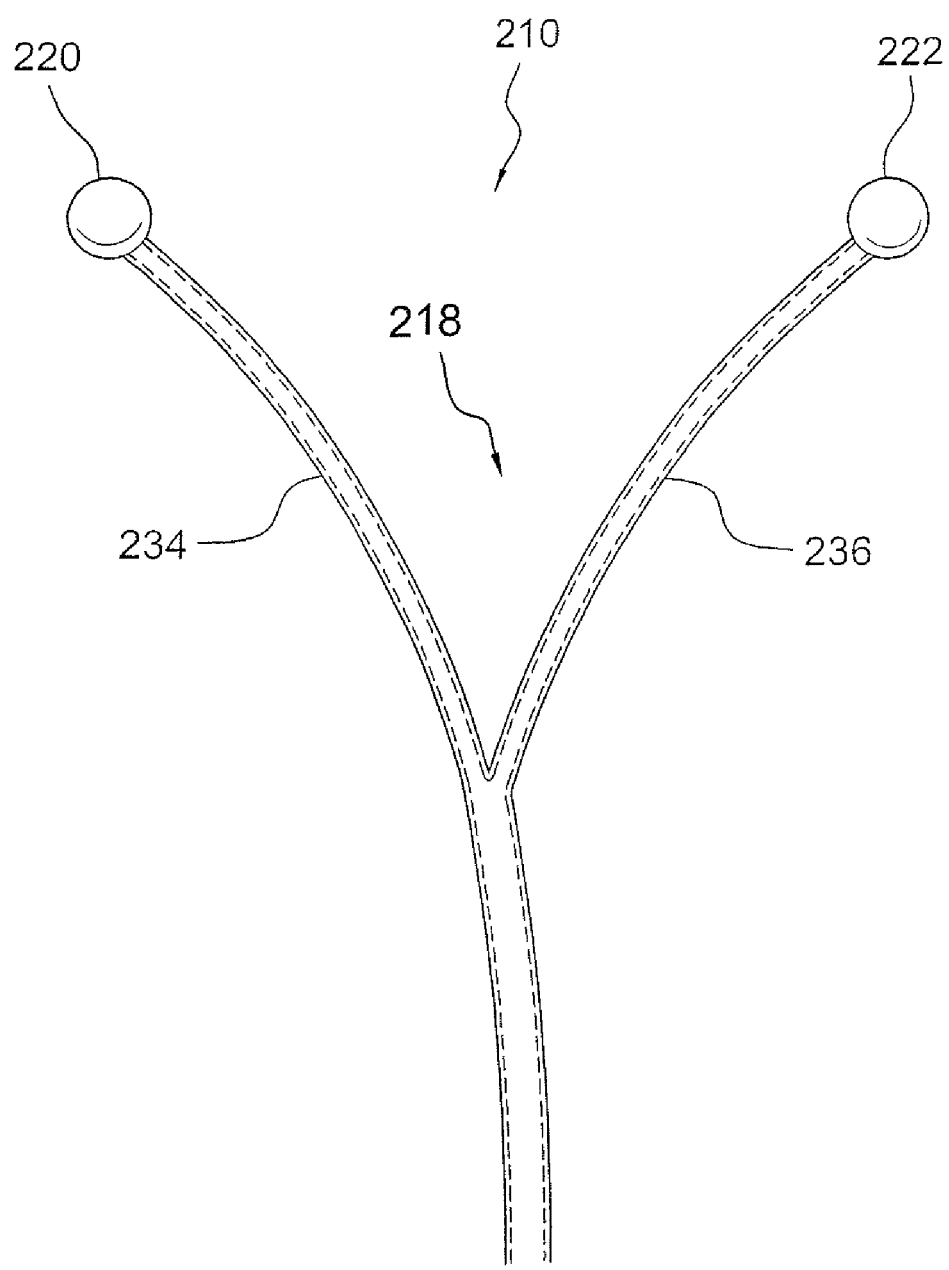
FIG. 39 is a schematic view of an alternate embodiment of an occlusion device in accordance with the present invention.

In accordance with an alternate embodiment and with reference to FIG. 39, the occlusion device 210 is provided with an elongated member 218 having hollow, tubular first and second legs 234, 236 allowing for the transport of an injectable material to the orifice plugs 220, 222. As such, and in accordance with this embodiment, the orifice plugs 220, 222 are made of a material (for example, a porous material) allowing transport of the injectable material from the first and second legs 234, 236, through the orifice plugs 220, 222 and to the selected tissue.

As those skilled in the art will certainly appreciate, a variety of embodiments have been disclosed above for implementation of the present invention. These various embodiments may be utilized alone or in combination, and various features may be combined to achieve results remaining within the spirit of the present invention.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An occlusion device for actively occluding fallopian tubes using the shape of a uterine cavity as a guide to proper positioning of the occlusion device, the occlusion device comprising:

a resilient body composed of a shape memory alloy, the resilient body including an elongated member having a first end and a second end, the elongated member further including a first leg ending with the first end of the elongated member, and a second leg ending with the second end of the elongated member and a connection member positioned therebetween;

a first orifice plug secured at the first end of the elongated member and a second orifice plug secured at the second end of the elongated member; and the first leg and the second leg are angularly oriented relative to each other such that the first leg and the second leg are allowed to move away from each other based upon the outward bias inherent in the resilient body and the resilience of the first leg and the second leg causing an outward bow in the first leg and the second leg when they are unrestrained;

wherein the first and second orifice plugs are shaped and dimensioned to seat at the orifices of the fallopian tubes or within the fallopian tubes when the elongated member spreads outwardly with the first end and second end moving apart until the first and second orifice plugs of the occlusion device distally reach respective walls of the uterine cavity, ride upon the walls of the uterine cavity and seat at the orifices of the fallopian tubes or within the fallopian tubes; and wherein the first and second orifice plugs are selectively separated from the resilient body.

2. The occlusion device according to claim 1, wherein the connection member is substantially circular with a first end connected to the first leg and a second end connected to the second leg.

3. The occlusion device according to claim 1, wherein the first orifice plug is spherical and the second orifice plug is spherical.

4. The occlusion device according to claim 1, wherein the first orifice plug and the second orifice plug each include a tissue in-growth member.

5. The occlusion device according to claim 4, wherein the tissue in-growth member is a fabric sock.

6. The occlusion device according to claim 1, wherein the first orifice plug and the second orifice plug each are impregnated with a medication.

7. The occlusion device according to claim 1, wherein the first orifice plug and the second orifice plug are shaped like a flying saucer.

8. The occlusion device according to claim 1 wherein the first orifice plug and the second orifice plug are football-shaped.

9. The occlusion device according to claim 1, wherein the first orifice plug and the second orifice plug are bell-shaped.

10. The occlusion device according to claim 1, wherein the first orifice plug and the second orifice plug each include multiple tapered ring members.

11. The occlusion device according to claim 1, wherein the first orifice plug and the second orifice plug each include a rounded tip and an outwardly tapering wall with a thin pliable flange at a proximal end thereof.

12. The occlusion device according to claim 1, wherein the first orifice plug and the second orifice plug each have a prolate spheroid shape.

13. The occlusion device according to claim 1, wherein the first orifice plug and the second orifice plug are each manufactured from an elastic material which swells upon placement in the fallopian tube.

14. The occlusion device according to claim 1, wherein the first orifice plug and the second orifice plug each include tissue in-growth promoting whiskers.

15. The occlusion device according to claim 1, wherein the first orifice plug and the second orifice plug each include tissue in-growth promoting loops.

16. An occlusion device for actively occluding fallopian tubes using the shape of a uterine cavity as a guide to proper positioning of the occlusion device, the occlusion device comprising:

a resilient body composed of a shape memory alloy, the resilient body including an elongated member having a first end and a second end, the elongated member further including a first leg ending with the first end of the elongated member, and a second leg ending with the second end of the elongated member and a connection member positioned therebetween;

a first orifice plug secured at the first end of the elongated member and a second orifice plug secured at the second end of the elongated member; and the first leg and the second leg are angularly oriented relative to each other such that the first leg and the second leg are allowed to move away from each other based upon the outward bias inherent in the resilient body and the resilience of the first leg and the second leg causing an outward bow in the first leg and the second leg when they are unrestrained;

wherein the first and second orifice plugs are shaped and dimensioned to seat at the orifices of the fallopian tubes or within the fallopian tubes when the elongated member spreads outwardly with the first end and second end moving apart until the first and second orifice plugs of the occlusion device distally reach respective walls of the uterine cavity, ride upon the walls of the uterine cavity and seat at the orifices of the fallopian tubes or within the fallopian tubes; and wherein the connection member is a spring biased loop.

17. The occlusion device according to claim 16, wherein the connection member is substantially circular with a first end connected to the first leg and a second end connected to the second leg.

18. The occlusion device according to claim 16, wherein the first orifice plug is spherical and the second orifice plug is spherical.

19. The occlusion device according to claim 16, wherein the first orifice plug and the second orifice plug each include a tissue in-growth member.

20. The occlusion device according to claim 19, wherein the tissue in-growth member is a fabric sock.

21. The occlusion device according to claim 16, wherein the first orifice plug and the second orifice plug each are impregnated with a medication.

22. The occlusion device according to claim 16, wherein the first orifice plug and the second orifice plug are shaped like a flying saucer.

23. The occlusion device according to claim 16, wherein the first orifice plug and the second orifice plug are football-shaped.

24. The occlusion device according to claim 16, wherein the first orifice plug and the second orifice plug are bell-shaped.

25. The occlusion device according to claim 16, wherein the first orifice plug and the second orifice plug each include multiple tapered ring members.

26. The occlusion device according to claim 16, wherein the first orifice plug and the second orifice plug each include a rounded tip and an outwardly tapering wall with a thin pliable flange at a proximal end thereof.

27. The occlusion device according to claim 16, wherein the first orifice plug and the second orifice plug each have a prolate spheroid shape.

28. The occlusion device according to claim 16, wherein the first orifice plug and the second orifice plug are each manufactured from an elastic material which swells upon placement in the fallopian tube.

29. The occlusion device according to claim 16, wherein the first orifice plug and the second orifice plug each include tissue in-growth promoting whiskers.

30. The occlusion device according to claim 16, wherein the first orifice plug and the second orifice plug each include tissue in-growth promoting loops.

31. An occlusion device for actively occluding fallopian tubes using the shape of a uterine cavity as a guide to proper positioning of the occlusion device, the occlusion device comprising:

a resilient body composed of a shape memory alloy, the resilient body including an elongated member having a first end and a second end, the elongated member further including a first leg ending with the first end of the elongated member, and a second leg ending with the second end of the elongated member and a connection member positioned therebetween;

a first orifice plug secured at the first end of the elongated member and a second orifice plug secured at the second end of the elongated member; and the first leg and the second leg are angularly oriented relative to each other such that the first leg and the second leg are allowed to move away from each other based upon the outward bias inherent in the resilient body and the resilience of the first leg and the second leg causing an outward bow in the first leg and the second leg when they are unrestrained;

wherein the first and second orifice plugs are shaped and dimensioned to seat at the orifices of the fallopian tubes or within the fallopian tubes when the elongated member spreads outwardly with the first end and second end moving apart until the first and second orifice plugs of the occlusion device distally reach respective walls of the uterine cavity, ride upon the walls of the uterine cavity and seat at the orifices of the fallopian tubes or within the fallopian tubes; and wherein the first orifice plug and the second orifice plug each include a ball and socket arrangement.

32. The occlusion device according to claim 31, wherein the connection member is substantially circular with a first end connected to the first leg and a second end connected to the second leg.

33. The occlusion device according to claim 31, wherein the first orifice plug is spherical and the second orifice plug is spherical.

34. The occlusion device according to claim 31, wherein the first orifice plug and the second orifice plug each include a tissue in-growth member.

35. The occlusion device according to claim 34, wherein the tissue in-growth member is a fabric sock.

36. The occlusion device according to claim 31, wherein the first orifice plug and the second orifice plug each are impregnated with a medication.

37. The occlusion device according to claim 31, wherein the first orifice plug and the second orifice plug are shaped like a flying saucer.

38. The occlusion device according to claim 31, wherein the first orifice plug and the second orifice plug are football-shaped.

39. The occlusion device according to claim 31, wherein the first orifice plug and the second orifice plug are bell-shaped.

40. The occlusion device according to claim 31, wherein the first orifice plug and the second orifice plug each include multiple tapered ring members.

41. The occlusion device according to claim 31, wherein the first orifice plug and the second orifice plug each include a rounded tip and an outwardly tapering wall with a thin pliable flange at a proximal end thereof.

42. The occlusion device according to claim 31, wherein the first orifice plug and the second orifice plug each have a prolate spheroid shape.

43. The occlusion device according to claim 31, wherein the first orifice plug and the second orifice plug are each manufactured from an elastic material which swells upon placement in the fallopian tube.

44. The occlusion device according to claim 31, wherein the first orifice plug and the second orifice plug each include tissue in-growth promoting whiskers.

45. The occlusion device according to claim 31, wherein the first orifice plug and the second orifice plug each include tissue in-growth promoting loops.

46. An occlusion device for actively occluding fallopian tubes using the shape of a uterine cavity as a guide to proper positioning of the occlusion device, the occlusion device comprising:
   a resilient body composed of a shape memory alloy, the resilient body including an elongated member having a first end and a second end, the elongated member further including a first leg ending with the first end of the elongated member, and a second leg ending with the second end of the elongated member and a connection member positioned therebetween;
   a first orifice plug secured at the first end of the elongated member and a second orifice plug secured at the second end of the elongated member; and
   the first leg and the second leg are angularly oriented relative to each other such that the first leg and the second leg are allowed to move away from each other based upon the outward bias inherent in the resilient body and the resilience of the first leg and the second leg causing an outward bow in the first leg and the second leg when they are unrestrained;
   wherein the first and second orifice plugs are shaped and dimensioned to seat at the orifices of the fallopian tubes or within the fallopian tubes when the elongated member spreads outwardly with the first end and second end moving apart until the first and second orifice plugs of the occlusion device distally reach respective walls of the uterine cavity, ride upon the walls of the uterine cavity and seat at the orifices of the fallopian tubes or within the fallopian tubes; and
   wherein the first orifice plug and the second orifice plug each include an inner portion made from a relatively hard material and an outer soft pliable material is affixed over the inner portion.

47. The occlusion device according to claim 46, wherein the connection member is substantially circular with a first end connected to the first leg and a second end connected to the second leg.

48. The occlusion device according to claim 46, wherein the first orifice plug is spherical and the second orifice plug is spherical.

49. The occlusion device according to claim 46, wherein the first orifice plug and the second orifice plug each include a tissue in-growth member.

50. The occlusion device according to claim 46, wherein the first orifice plug and the second orifice plug each are impregnated with a medication.

51. The occlusion device according to claim 46, wherein the first orifice plug and the second orifice plug are shaped like a flying saucer.

52. The occlusion device according to claim 46, wherein the first orifice plug and the second orifice plug are football-shaped.

53. The occlusion device according to claim 46, wherein the first orifice plug and the second orifice plug are bell-shaped.

54. The occlusion device according to claim 46, wherein the first orifice plug and the second orifice plug each include multiple tapered ring members.

55. The occlusion device according to claim 46, wherein the first orifice plug and the second orifice plug each include a rounded tip and an outwardly tapering wall with a thin pliable flange at a proximal end thereof.

56. The occlusion device according to claim 46, wherein the first orifice plug and the second orifice plug each have a prolate spheroid shape.

57. The occlusion device according to claim 46, wherein the first orifice plug and the second orifice plug are each manufactured from an elastic material which swells upon placement in the fallopian tube.

58. The occlusion device according to claim 46, wherein the first orifice plug and the second orifice plug each include tissue in-growth promoting whiskers.

59. The occlusion device according to claim 46, wherein the first orifice plug and the second orifice plug each include tissue in-growth promoting loops.

60. An occlusion device for actively occluding fallopian tubes using the shape of a uterine cavity as a guide to proper positioning of the occlusion device, the occlusion device comprising:
   a resilient body composed of a shape memory alloy, the resilient body including an elongated member having a first end and a second end, the elongated member further including a first leg ending with the first end of the elongated member, and a second leg ending with the second end of the elongated member and a connection member positioned therebetween;
   a first orifice plug secured at the first end of the elongated member and a second orifice plug secured at the second end of the elongated member; and
   the first leg and the second leg are angularly oriented relative to each other such that the first leg and the second leg are allowed to move away from each other based upon the outward bias inherent in the resilient body and the resilience of the first leg and the second leg causing an outward bow in the first leg and the second leg when they are unrestrained;
   wherein the first and second orifice plugs are shaped and dimensioned to seat at the orifices of the fallopian tubes or within the fallopian tubes when the elongated member spreads outwardly with the first end and second end moving apart until the first and second orifice plugs of the occlusion device distally reach respective walls of the uterine cavity, ride upon the walls of the uterine cavity and seat at the orifices of the fallopian tubes or within the fallopian tubes; and
   wherein the first orifice plug and the second orifice plug each include a hard outer shell composed of a bioabsorbable material which quickly dissolves upon deployment within the fallopian tube.

61. The occlusion device according to claim 60, wherein the connection member is substantially circular with a first end connected to the first leg and a second end connected to the second leg.

62. The occlusion device according to claim 60, wherein the first orifice plug is spherical and the second orifice plug is spherical.

63. The occlusion device according to claim 60, wherein the first orifice plug and the second orifice plug each include a tissue in-growth member.

64. The occlusion device according to claim 60, wherein the first orifice plug and the second orifice plug each are impregnated with a medication.

65. The occlusion device according to claim 60, wherein the first orifice plug and the second orifice plug are shaped like a flying saucer.

66. The occlusion device according to claim 60, wherein the first orifice plug and the second orifice plug are football-shaped.

67. The occlusion device according to claim 60, wherein the first orifice plug and the second orifice plug are bell-shaped.

68. The occlusion device according to claim 60, wherein the first orifice plug and the second orifice plug each include multiple tapered ring members.

69. The occlusion device according to claim 60, wherein the first orifice plug and the second orifice plug each include a rounded tip and an outwardly tapering wall with a thin pliable flange at a proximal end thereof.

70. The occlusion device according to claim 60, wherein the first orifice plug and the second orifice plug each have a prolate spheroid shape.

71. The occlusion device according to claim 60, wherein the first orifice plug and the second orifice plug are each manufactured from an elastic material which swells upon placement in the fallopian tube.

72. The occlusion device according to claim 60, wherein the first orifice plug and the second orifice plug each include tissue in-growth promoting whiskers.

73. The occlusion device according to claim 60, wherein the first orifice plug and the second orifice plug each include tissue in-growth promoting loops.

\* \* \* \* \*

UNITED STATES PATENT AND TRADEMARK OFFICE
CERTIFICATE OF CORRECTION

PATENT NO. : 7,621,276 B2  Page 1 of 1
APPLICATION NO. : 11/892560
DATED : November 24, 2009
INVENTOR(S) : Michael N. Tal et al.

It is certified that error appears in the above-identified patent and that said Letters Patent is hereby corrected as shown below:

On the Title page, item 73 the second Assignee's name is misspelled. The Assignee is Contramed, LLC, not Cantramed, LLC.

Signed and Sealed this

Twenty-sixth Day of January, 2010

David J. Kappos
*Director of the United States Patent and Trademark Office*